US009480549B2

(12) United States Patent
Samaniego

(10) Patent No.: US 9,480,549 B2
(45) Date of Patent: Nov. 1, 2016

(54) MULTI-LAYER TISSUE PATCHES

(71) Applicant: AlloSource, Centennial, CO (US)

(72) Inventor: Adrian C. Samaniego, Parker, CO (US)

(73) Assignee: AlloSource, Centennial, CO (US)

( * ) Notice: Subject to any disclaimer, the term of this patent is extended or adjusted under 35 U.S.C. 154(b) by 703 days.

(21) Appl. No.: 13/793,331

(22) Filed: Mar. 11, 2013

(65) Prior Publication Data

US 2013/0204393 A1    Aug. 8, 2013

Related U.S. Application Data

(63) Continuation-in-part of application No. 13/186,661, filed on Jul. 20, 2011.

(60) Provisional application No. 61/388,986, filed on Oct. 1, 2010.

(51) Int. Cl.
*A61F 2/02* (2006.01)
*A61L 27/36* (2006.01)
(Continued)

(52) U.S. Cl.
CPC ............ *A61F 2/02* (2013.01); *A61L 27/3604* (2013.01); *A61L 27/3687* (2013.01); *A61F 2/105* (2013.01); *A61K 35/50* (2013.01); *A61L 26/0061* (2013.01); *A61L 27/00* (2013.01)

(58) Field of Classification Search
CPC ............ A61F 2/00; A61F 2/02; A61F 2/105; A61K 35/50; A61L 27/00; A61L 27/36; A61L 27/3604; A61L 27/60; A61L 27/362; A61L 27/3641; A61L 27/3666; A61L 27/38; A61L 27/3808; A61L 27/3813; A61L 27/3839; A61L 27/3869; A61L 26/0061; A61L 26/0095; A61L 26/0085; A61L 26/0042
See application file for complete search history.

(56) References Cited

U.S. PATENT DOCUMENTS 4,120,649 A    10/1978    Schechter
4,361,552 A    11/1982    Baur, Jr.
(Continued)

FOREIGN PATENT DOCUMENTS

EP    0 285 370 A2    5/1988
EP    0 669 138 A2    8/1995
(Continued)

OTHER PUBLICATIONS

Extended European Search Report for European Patent Application No. 11829728.2, dated May 21, 2014, all pages.
(Continued)

*Primary Examiner* — Julian W Woo
*Assistant Examiner* — Lucas Paez
(74) *Attorney, Agent, or Firm* — Kilpatrick Townsend & Stockton LLP

(57) ABSTRACT

Embodiments of the present invention encompass anti-adhesion wound dressings including patches made from amnion tissue obtained from human birth tissue. Exemplary amnion patches can be fabricated by folding a section of amnion over on itself with the epithelial layer on the outside of the folded patch and the fibroblast layer on the inside of the folded patch. Optionally, individual amnion tissue pieces can be sandwiched together to provide a multi-layer patch. Sufficient pressure is applied to the layered amnion to cause adherence between opposing faces of the fibroblast layers. The pressed fibroblast layers provide mechanical strength to hold the amnion patch together with the epithelial layers on the outsides of the amnion patch.

17 Claims, 16 Drawing Sheets

(51) Int. Cl.
*A61F 2/10* (2006.01)
*A61K 35/50* (2015.01)
*A61L 26/00* (2006.01)
*A61L 27/00* (2006.01)

(56) References Cited

U.S. PATENT DOCUMENTS

| | | |
|---|---|---|
| 5,336,616 A | 8/1994 | Livesey et al. |
| 5,607,590 A | 3/1997 | Shimizu |
| 5,618,312 A | 4/1997 | Yui et al. |
| 5,723,010 A | 3/1998 | Yui et al. |
| 5,837,278 A | 11/1998 | Geistlich et al. |
| 5,876,451 A | 3/1999 | Yui et al. |
| 5,879,383 A * | 3/1999 | Bruchman ............ A61L 27/16 623/1.44 |
| 5,916,266 A | 6/1999 | Yui et al. |
| 5,989,498 A | 11/1999 | Odland |
| 6,152,142 A | 11/2000 | Tseng |
| 6,326,019 B1 | 12/2001 | Tseng |
| 6,432,710 B1 | 8/2002 | Boss |
| 6,576,618 B1 | 6/2003 | Herndon et al. |
| 6,783,776 B2 | 8/2004 | Spievack |
| 7,347,876 B2 | 3/2008 | Tsai |
| 7,393,437 B2 | 7/2008 | Chan |
| 7,494,802 B2 | 2/2009 | Tseng |
| 7,723,108 B2 | 5/2010 | Truncale et al. |
| 7,727,550 B2 | 6/2010 | Siegal et al. |
| 7,775,965 B2 | 8/2010 | McFetridge |
| 7,824,671 B2 | 11/2010 | Binder |
| 7,902,145 B2 | 3/2011 | Chu |
| 7,972,852 B2 | 7/2011 | Mochitate |
| 8,021,692 B2 | 9/2011 | Hiles |
| 8,058,066 B2 | 11/2011 | Marshall |
| 8,071,135 B2 | 12/2011 | Liu et al. |
| 8,105,634 B2 | 1/2012 | Liu et al. |
| 8,153,162 B2 | 4/2012 | Tseng |
| 8,158,141 B2 | 4/2012 | Chen |
| 8,182,840 B2 | 5/2012 | Tseng |
| 8,182,841 B2 | 5/2012 | Tseng |
| 8,187,639 B2 | 5/2012 | Tseng |
| 8,198,245 B2 | 6/2012 | Niklason |
| 8,231,908 B2 | 7/2012 | Kinoshita |
| 8,323,701 B2 | 12/2012 | Daniel et al. |
| 8,357,403 B2 | 1/2013 | Daniel et al. |
| 8,372,437 B2 | 2/2013 | Daniel |
| 8,372,438 B2 | 2/2013 | Daniel et al. |
| 8,372,439 B2 | 2/2013 | Daniel et al. |
| 8,409,626 B2 | 4/2013 | Daniel et al. |
| 8,420,126 B2 | 4/2013 | Tseng |
| 8,440,235 B2 | 5/2013 | Tseng |
| 8,455,009 B2 | 6/2013 | Tseng et al. |
| 8,460,714 B2 | 6/2013 | Tseng et al. |
| 8,460,715 B2 | 6/2013 | Daniel |
| 8,460,716 B2 | 6/2013 | Daniel |
| 8,597,687 B2 | 12/2013 | Daniel et al. |
| 8,623,421 B2 | 1/2014 | Daniel |
| 8,642,092 B2 | 2/2014 | Daniel et al. |
| 8,703,206 B2 | 4/2014 | Daniel et al. |
| 8,703,207 B2 | 4/2014 | Daniel et al. |
| 8,709,493 B2 | 4/2014 | Daniel et al. |
| 8,709,494 B2 | 4/2014 | Daniel |
| 8,822,415 B2 | 9/2014 | Trumpower et al. |
| 8,883,210 B1 | 11/2014 | Truncale et al. |
| 8,904,664 B2 | 12/2014 | Pringle et al. |
| 8,932,643 B2 | 1/2015 | Daniel et al. |
| 8,940,684 B2 | 1/2015 | Koob |
| 8,946,163 B2 | 2/2015 | Koob |
| 9,358,320 B2 | 6/2016 | Samaniego et al. |
| 2003/0060695 A1 | 3/2003 | Connelly |
| 2003/0187515 A1 | 10/2003 | Hariri et al. |
| 2004/0048796 A1 | 3/2004 | Hariri et al. |
| 2005/0019865 A1 | 1/2005 | Kihm |
| 2005/0058631 A1 | 3/2005 | Kihm |
| 2005/0220848 A1 | 10/2005 | Bates |
| 2006/0153928 A1 | 7/2006 | Kinoshita et al. |
| 2006/0234376 A1 | 10/2006 | Mistry |
| 2007/0015278 A1 | 1/2007 | Li et al. |
| 2007/0020320 A1 | 1/2007 | David et al. |
| 2007/0160588 A1 | 7/2007 | Kihm |
| 2007/0254013 A1 | 11/2007 | Taguchi et al. |
| 2008/0039940 A1 | 2/2008 | Hashimoto et al. |
| 2008/0044848 A1 | 2/2008 | Heidaran |
| 2008/0046095 A1 | 2/2008 | Daniel |
| 2008/0069895 A1 | 3/2008 | Liu et al. |
| 2008/0113007 A1 | 5/2008 | Kurihara et al. |
| 2008/0131522 A1 | 6/2008 | Liu et al. |
| 2008/0193554 A1 | 8/2008 | Dua et al. |
| 2009/0053279 A1* | 2/2009 | Badylak ............ A61L 27/3683 424/423 |
| 2009/0258082 A1 | 10/2009 | Nikaido et al. |
| 2009/0275011 A1 | 11/2009 | Eibl et al. |
| 2010/0104539 A1 | 4/2010 | Daniel et al. |
| 2010/0112543 A1 | 5/2010 | Ngo |
| 2010/0196478 A1 | 8/2010 | Masters |
| 2010/0304487 A1 | 12/2010 | Truncale |
| 2011/0020420 A1 | 1/2011 | Bosley et al. |
| 2011/0091434 A1 | 4/2011 | Miller |
| 2011/0104100 A1 | 5/2011 | Riordan |
| 2011/0129520 A1 | 6/2011 | Bogdansky et al. |
| 2011/0160857 A1 | 6/2011 | Bracone |
| 2011/0206776 A1 | 8/2011 | Tom et al. |
| 2011/0256202 A1 | 10/2011 | Tom et al. |
| 2011/0262393 A1 | 10/2011 | Yang |
| 2011/0307059 A1 | 12/2011 | Young et al. |
| 2012/0009644 A1 | 1/2012 | Hamby et al. |
| 2012/0009679 A1 | 1/2012 | Hamby et al. |
| 2012/0010708 A1 | 1/2012 | Young et al. |
| 2012/0010725 A1 | 1/2012 | Hamby et al. |
| 2012/0010727 A1 | 1/2012 | Young et al. |
| 2012/0016491 A1 | 1/2012 | Matheny |
| 2012/0063997 A1 | 3/2012 | Hunter |
| 2012/0078378 A1 | 3/2012 | Daniel et al. |
| 2012/0083900 A1 | 4/2012 | Samaniego et al. |
| 2012/0141595 A1 | 6/2012 | Tseng et al. |
| 2012/0142102 A1 | 6/2012 | Chen |
| 2012/0164114 A1 | 6/2012 | Abbot |
| 2012/0189583 A1 | 7/2012 | Liu et al. |
| 2012/0189586 A1 | 7/2012 | Harrell |
| 2012/0191184 A1 | 7/2012 | Chen |
| 2012/0201787 A1 | 8/2012 | Abbot |
| 2012/0225484 A1 | 9/2012 | Bhatia et al. |
| 2012/0269774 A1 | 10/2012 | Ichim |
| 2012/0276080 A1 | 11/2012 | Kinoshita et al. |
| 2012/0294810 A1 | 11/2012 | Daniel |
| 2012/0294811 A1 | 11/2012 | Daniel |
| 2012/0294908 A1 | 11/2012 | Daniel et al. |
| 2012/0294910 A1 | 11/2012 | Daniel et al. |
| 2012/0328690 A1 | 12/2012 | Tseng et al. |
| 2013/0004465 A1 | 1/2013 | Aberman |
| 2013/0006385 A1 | 1/2013 | Daniel |
| 2013/0052169 A1 | 2/2013 | Marom |
| 2013/0202676 A1 | 8/2013 | Koob et al. |
| 2013/0218274 A1 | 8/2013 | Spencer et al. |
| 2013/0230561 A1 | 9/2013 | Daniel et al. |
| 2013/0247517 A1 | 9/2013 | Samaniego et al. |
| 2013/0344162 A1 | 12/2013 | Morse et al. |
| 2014/0012393 A1 | 1/2014 | Shin et al. |
| 2014/0017280 A1 | 1/2014 | Daniel et al. |
| 2014/0037598 A1 | 2/2014 | Jansen et al. |
| 2014/0050788 A1 | 2/2014 | Daniel et al. |
| 2014/0052247 A1 | 2/2014 | Daniel et al. |
| 2014/0052274 A1 | 2/2014 | Koob et al. |
| 2014/0106447 A1 | 4/2014 | Brown et al. |
| 2014/0127177 A1 | 5/2014 | Tom et al. |
| 2014/0140964 A1 | 5/2014 | Brown et al. |
| 2014/0205646 A1 | 7/2014 | Morse et al. |
| 2014/0214176 A1 | 7/2014 | Daniel et al. |
| 2014/0234387 A1 | 8/2014 | Daniel et al. |
| 2014/0255496 A1 | 9/2014 | Daniel et al. |
| 2014/0255508 A1 | 9/2014 | Morse et al. |
| 2015/0010506 A1 | 1/2015 | Jansen et al. |
| 2015/0140114 A1 | 5/2015 | Sasko |

(56) References Cited

U.S. PATENT DOCUMENTS

2015/0174297 A1 6/2015 Daniel
2015/0209475 A1 7/2015 Daniel
2015/0265747 A1 9/2015 Daniel

FOREIGN PATENT DOCUMENTS

WO 03/084410 A1 10/2003
WO 2009/132186 10/2009

OTHER PUBLICATIONS

Ferguson II, et al.: "Abundant expression of parathyroid hormone-related protein in human amnion and its association with labor", Proc. Natl. Acad. Sci.USE Physiology, vol. 89, 1992, pp. 8384-8388.
International Preliminary Report on Patentability of PCT/US11/47518, issued Apr. 23, 2013, all pages.
International Search Report and Written Opinion of PCT/US11/47518, mailed Dec. 15, 2011, all pages.
Gruss, J., et al., "Human amniotic membrane: a versatile wound dressing," Canadian Medical Association Journal, vol. 118, May 20, 1978, pp. 1237-1246.
International Preliminary Report on Patentability of PCT/US2009/041534 mailed on Oct. 26, 2010 6 pages.
International Search Report and Written Opinion of PCT/US2009/041534 mailed on Jun. 17, 2009, 7 pages.
Kim, S., et al., "Use of human amniotic membrane wrap in reducing perineural adhesions in a rabbit model of ulnar nerve neurorrhaphy," Journal of Hand Surgery, (European), Dec. 9, 2009, 0: 0:, pp. 1-6.
Spoerl, E., et al., "Cross-Linking of Human Amniotic Membrane by Glutaraldehyde," Ophthalmic Research, vol. 36, 2004, pp. 71-77.
Tao, H., et al., "Implantation of amniotic membrane to reduce postlaminectomy epidural adhesions," European Spine Journal, vol. 18(8), Aug. 2009, pp. 1202-1212.
Extended European Search Report for EP Patent Application No. 09734434.5, mailed on Jul. 28, 2011, all pages.

* cited by examiner

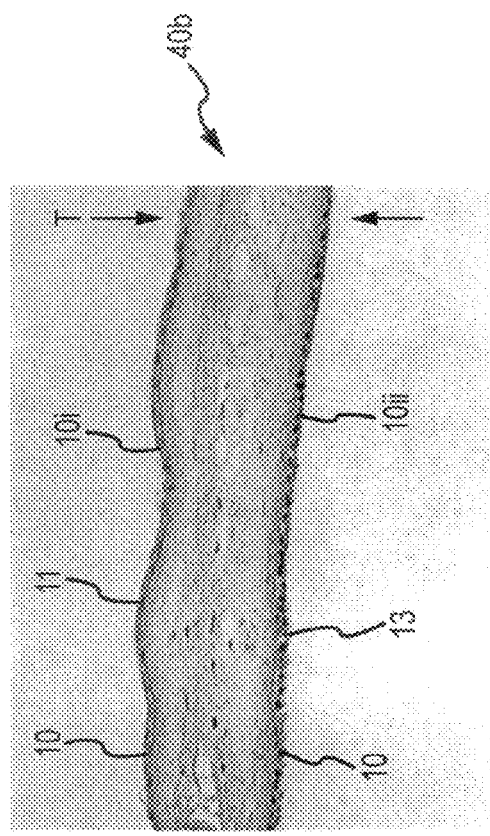
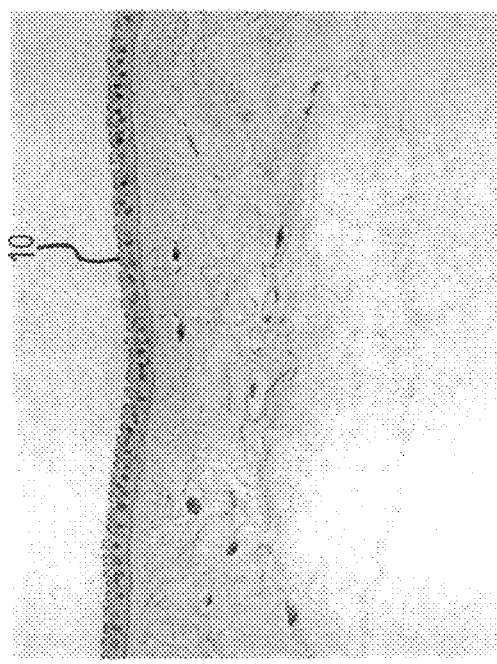
FIG. 4B
FIG. 4A

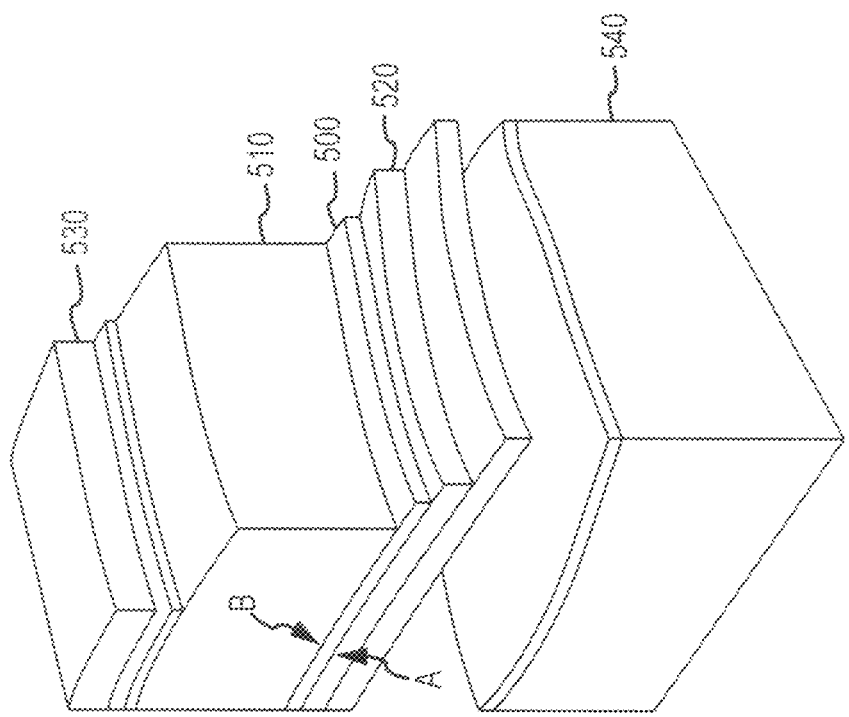
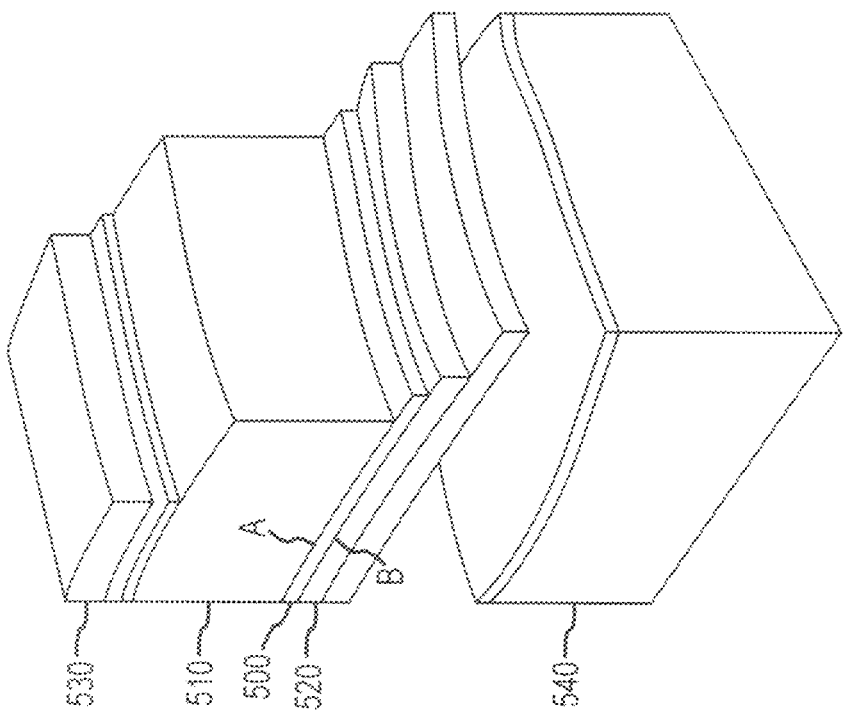
FIG.5A
FIG.5B

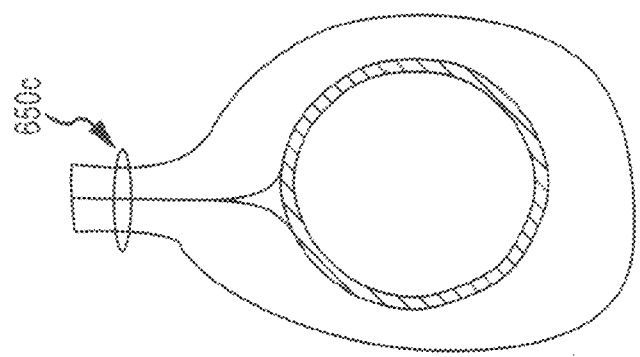
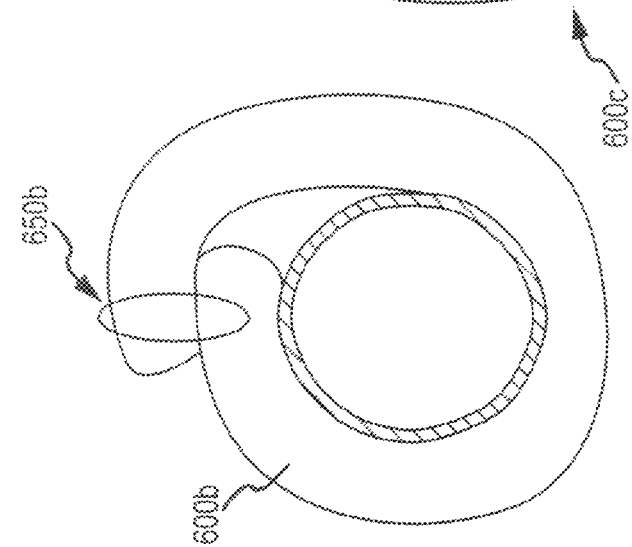
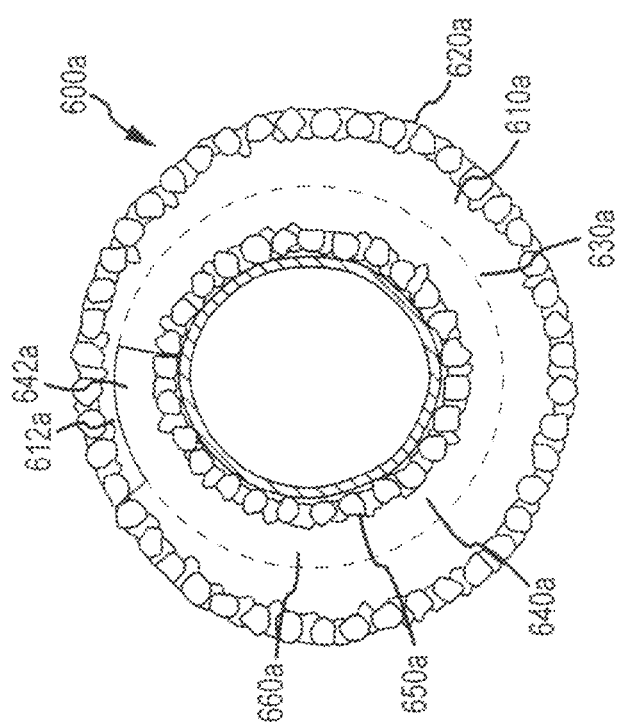

MULTI-LAYER TISSUE PATCHES

CROSS-REFERENCES TO RELATED APPLICATIONS

This application is a continuation-in-part of U.S. patent application Ser. No. 13/186,661, filed Jul. 20, 2011, which is a nonprovisional of, and claims the benefit of priority to, U.S. Provisional Patent Application No. 61/388,986 filed Oct. 1, 2010. This application is also related to U.S. Provisional Patent Application No. 61/047,842 filed Apr. 25, 2008 and U.S. patent application Ser. No. 12/428,836 filed Apr. 23, 2009. The entire content of each of the above filings is incorporated herein by reference.

BACKGROUND OF THE INVENTION

Embodiments of the present invention are directed in general to the field of medical dressings, and in particular to multi-layer tissue compositions, and methods of their use and manufacture.

Human birth tissue can be defined as the amniotic sac (which includes two tissue layers, the amnion and chorion), the placenta, the umbilical cord, and the cells and fluid contained in each. Human amniotic membrane has been used for many years in various surgical procedures, including skin transplantation and ocular surface disorder treatments to prevent adhesions. Relatedly, certain known medical techniques involve the application of amnion tissue to patients in the form of surgical dressings. For example, amniotic surgical wound dressings are described in WO 2009/132186, the content of which is incorporated herein by reference. Although amniotic compositions and methods are presently available and provide real benefits to patients in need thereof, many advances may still be made to provide improved dressing systems and methods for treating patients. The dressing systems and treatment and manufacture methods described herein provide further solutions and answers to these outstanding needs.

BRIEF SUMMARY OF THE INVENTION

Embodiments of the present invention encompass back-to-back tissue patches or dressings, and method for their use and manufacture. In some instances, embodiments provide multi-layer tissue compositions that present epithelial layer surfaces on two opposing sides of a dressing. Such dressings are well suited for use as nerve wraps, tendon wraps, bone defect overlays, and the like. Relatedly, such dressings can be used to treat patients having tarsal tunnel syndrome, iliotibial band stenosis, phantom pain associated with amputation, damaged meniscus, peripheral nerve damage or injuries, and the like. Further, dressings can be used in spinal treatments including laminectomies, anterior lumbar interbody fusion (ALIF) procedures, laminotomies, and in extensor halgus longus tendon surgeries. Shortly following any surgery or trauma, fibrotic infiltration may be initiated, thus resulting in fibrin becoming deposited at the surgical or trauma site and organized into fibrous adhesions. Use of multi-layer amnion dressings according to embodiments of the present invention can prevent or inhibit the development of such adhesions.

In one aspect, embodiments of the present invention include methods of manufacturing a multi-layer amnion tissue patch. Exemplary methods may include obtaining a first amnion layer having an epithelial layer, a basement membrane, a compact layer, and a fibroblast layer, obtaining a second amnion layer having an epithelial layer, a basement membrane, a compact layer, and a fibroblast layer, approximating the first and second amnion layers, and processing the first and second amnion layers so that at least a portion of the fibroblast layer of the first amnion layer is operatively associated with or adhered with at least a portion of the fibroblast layer of the second amnion layer, so as to form an intertwined or mated fibroblast region disposed between the epithelial layer of the first amnion layer and the epithelial layer of the second amnion layer. Relatedly, exemplary methods may include obtaining an amnion tissue having a first portion and a second portion, and folding the amnion tissue over on itself so that the first portion at least partially overlaps the second portion to provide a first amnion layer and a second amnion layer, each of the first and second amnion layers having an epithelial layer, a basement membrane, a compact layer, and a fibroblast layer. Such methods may also include processing the folded amnion tissue so that at least a portion of the fibroblast layer of the first amnion layer is operatively associated or adhered with at least a portion of the fibroblast layer of the second amnion layer so as to form an intertwined or mated fibroblast region disposed between the epithelial layer of the first amnion layer and the epithelial layer of the second amnion layer.

In another aspect, embodiments of the present invention encompass multi-layer patches which may include, for example, a first tissue layer having an epithelial layer and a basement membrane, and a second tissue layer having an epithelial layer and a basement membrane. The epithelial layers of the first and second tissue layers can define first and second opposing outer surfaces of the patch, respectively. In some cases, each of the first and second tissue layers comprise an amnion tissue layer. In some cases, the amnion layer of the first tissue layer includes a fibroblast layer, the amnion layer of the second tissue layer includes a fibroblast layer, and at least a portion of the fibroblast layer of the first amnion layer is coupled with at least a portion of the fibroblast layer of the second amnion layer. In some cases, at least a portion of a fibroblast layer of the first amnion layer is coupled with at least a portion of a fibroblast layer of the second amnion layer so as to form an interface disposed between the epithelial layer of the first amnion layer and the epithelial layer of the second amnion layer. In some cases, the first amnion layer includes a fibroblast layer and a compact layer disposed between the fibroblast layer and the basement membrane, and the second amnion layer includes a fibroblast layer and a compact layer disposed between the fibroblast layer and the basement membrane.

According to some embodiments, each of the first and second tissue layers may include an amnion tissue layer, an intestine tissue layer, or an umbilical cord tissue layer. Optionally, the first layer can be connected with the second layer via a fold. In some instances, the patch has a thickness within a range from about 40 microns to about 500 microns. In some instances, the patch has a thickness within a range from about 70 microns to about 200 microns. Optionally, the patch can be sterilized. Exemplary patches may also include a backing material placed on the first tissue layer, the second tissue layer, or both. In some instances, the patch has a tensile strength with a range from about 3.3 MPa to about 36.4 MPa. In some instances, the patch has a tensile strength with a range from about 6.6 MPa to about 18.2 MPa. In some instances, the patch has a 4.0 suture pullout force with a range from about 0.40 N to about 0.70 N. According to some embodiments, the first tissue layer is disposed in a first orientation, and the second tissue layer is disposed in a second orientation that is angularly offset from the first orientation. Optionally, the first orientation can be angularly offset from the second orientation by about 90 degrees. In some instances, the patch has a tensile strength within a range from about 9 MPa to about 47.2 MPa. In some instances, the patch has a tensile strength within a range from about 18 MPa to about 23.6 MPa. In some instances, the mated or compressed portions of first and second fibroblast layers remain coupled when the patch is suspended in a saline solution. Optionally, either or both of the first and second tissue layers can treated with glutaraldehyde.

In another aspect, embodiments of the present invention encompass methods of manufacturing multi-layer tissue patches which may include contacting a first tissue layer having an epithelial layer and a basement membrane with a second tissue layer having an epithelial layer and a basement membrane so as to form the patch, such that the epithelial layers of the first and second tissue layers define first and second opposing outer surfaces of the patch, respectively. In some cases, the first tissue layer and the second tissue layer are each part of a single piece of tissue, and the contacting step or manufacturing method may include folding the single piece of tissue over on itself so that a portion of the first tissue layer at least partially overlaps a portion of the second tissue layer. In some cases, the first tissue layer and the second tissue layer are each separate pieces of tissue, and the contacting step or manufacturing method may include approximating the first and second layers so that a portion of the first tissue layer at least partially overlaps a portion of the second tissue layer. In some cases, upon approximation the first tissue layer is disposed in a first orientation, and the second tissue layer is disposed in a second orientation that is angularly offset from the first orientation. For example, the first orientation can be angularly offset from the second orientation by about 90 degrees.

According to some embodiments, each of the first and second tissue layers includes a fibroblast layer, and the contacting step or manufacturing methods includes approximating the first and second tissue layers such that at least a portion of the fibroblast layer of the first tissue layer is mated with at least a portion of the fibroblast layer of the second tissue layer, so as to form a fibroblast region disposed between the epithelial layer of the first tissue layer and the epithelial layer of the second tissue layer. Optionally, each of the first and second tissue layers comprise an amnion tissue layer. In some instances, each of the first and second tissue layers can be an amnion tissue layer, an intestine tissue layer, or an umbilical cord tissue layer. Optionally, the manufacturing method may include treating the first and second tissue layers with a 1% glutaraldehyde solution for a period of up to 15 minutes. In some instances, manufacturing methods may include pressing the first tissue layer and the second tissue layer against each other. For example, the first tissue layer and the second tissue layer can be pressed against each other with a press apparatus. In some instances, the first tissue layer and the second tissue layer are pressed against each other with a force within a range from about 10 psi to about 400 psi. In some instances, the first tissue layer and the second tissue layer are pressed against each other with a force within a range from about 20 psi to about 50 psi. In some instances, the first tissue layer and the second tissue layer are pressed against each other for a duration within a range from about 5 seconds to about 24 hours. In some instances, the first tissue layer and the second tissue layer are pressed against each other for a duration within a range from about 30 seconds to about 12 hours. Optionally, the first tissue layer and the second tissue layer can be pressed against each other with a force of about 40 psi for a duration of about 15 minutes.

In yet another aspect, embodiments of the present invention encompass methods of treating a patient with a multi-layer tissue patch. Exemplary methods may include obtaining a multi-layer tissue patch that has a first tissue layer with an epithelial layer and a basement membrane, and a second tissue layer with an epithelial layer and a basement membrane. The epithelial layers of the first and second tissue layers can define first and second opposing outer surfaces of the patch, respectively. Methods further include administering the multi-layer tissue patch to the patient. In some cases, the multi-layer issue patch is administered to a surgical site within or on the patient's body. In some cases, the multi-layer tissue patch is administered to a trauma site within or on the patient's body. In some cases, the multi-layer tissue patch is administered to a patient tissue that is injured, damaged, crushed, sutured, inflamed, or ligated. Exemplary methods may also include positioning the multi-layer tissue patch between opposing anatomical structures within the patient. Some methods may involve positioning the multi-layer tissue patch about one or more an anatomical structures within the patient. According to some method embodiments, the administration step may involve coupling the tissue patch to the patient. In some instances, the administering step may include suturing the tissue patch to the patient. In some instances, the administering step may include placing one or more staples, sutures, ties, pins, or the like, in the tissue patch, so as to bind or hold portions of the patch together.

According to some embodiments, the administering step may include wrapping the patch about a patient nerve, wrapping the patch about a patient tendon, onlaying the patch over a patient bone defect, placing the patch within a patient tarsal tunnel, applying the patch to the patient's spine during a laminectomy procedure, applying the patch to the patient's spine during an anterior lumbar interbody fusion procedure, applying the patch to the patient's spine during a laminotomy procedure, contacting the patch with a patient peripheral nerve, contacting the patch with a patient iliotibial band, contacting the patch with a patient meniscus, or contacting the patch with a patient extensor halgus longus tendon. In some instances, either or both of the first and second layers are treated with glutaraldehyde. In some instances, each of the first and second tissue layers includes an amnion tissue layer. In some instances, the amnion layer of the first tissue layer includes a fibroblast layer, the amnion layer of the second tissue layer includes a fibroblast layer, and at least a portion of the fibroblast layer of the first amnion layer is coupled with at least a portion of the fibroblast layer of the second amnion layer. In some instances, at least a portion of a fibroblast layer of the first amnion layer is coupled with at least a portion of a fibroblast layer of the second amnion layer so as to form an interface disposed between the epithelial layer of the first amnion layer and the epithelial layer of the second amnion layer. In some instances, the first amnion layer includes a fibroblast layer and a compact layer disposed between the fibroblast layer and the basement membrane, and the second amnion layer includes a fibroblast layer and a compact layer disposed between the fibroblast layer and the basement membrane. In some instances, each of the first and second tissue layers include an amnion tissue layer, an intestine tissue layer, or an umbilical cord tissue layer.

Hence, embodiments of the present invention are directed, in some aspects, to anti-adhesion wound dressings including patches made from amnion tissue obtained from human birth tissue. The amnion patches can be fabricated by folding a section of amnion over on itself with the epithelial layer on the outside of the folded patch and the fibroblast layer on the inside of the folded patch. Optionally, two separate amnion layer pieces, which are not connected via a fold, can be approximated or placed next to each other. Sufficient pressure can be applied to the folded amnion to cause the fibers of the opposing faces of the fibroblast layers to become adhered. The adhered fibroblast layers provide mechanical strength to hold the amnion patch together with the epithelial layers on the outside of the amnion patch.

In some embodiments, adjacent amnion layers can be bonded with any of a variety of glues, adhesives, bonding agents, or cements. For example, amnion layers can be coupled together using cyanoacrylate based adhesives such as methyl 2-cyanoacrylate, ethyl-2-cyanoacrylate, n-butyl cyanoacrylate, 2-octyl cyanoacrylate, or the like. Similarly, medical adhesives, skin glues, biological glues, and related products may be used to bond amnion layers together. In some cases, amnion layers can be coupled together using fibrin glues such as Tisseel. In some cases, amnion layers can be joined using dental polymers such as resin ionomer cement which is cured with blue UV light. In some cases, a gelatin solution or a collagen solution can be used to adhere multiple amnion layers together.

When placed within a patient, multi-layer amnion dressings can operate as barrier agents between opposing anatomical structures during tissue healing, to prevent or inhibit formation of adhesions. For example, multi-layer amnion dressings can be used in gynecological procedures to prevent or inhibit the formation of pelvic, uterine, or ovarian adhesions, and the like. Other adhesions such as those around a tendon resection or nerve wrap adhesions are somewhat similar in that they all involve inflammatory response and the presence of a cellular fibrotic response and fibrinogen/fibrin. Hence, multi-layer amnion dressings can be used in these indications as well. A typical tendon interface adhesion usually involves a scarring response, and multi-layer dressings can be used to prevent or inhibit such adhesions to tendons. Generally, adhesions are a common consequence of surgery, including abdominal and pelvic surgery. Thus, surgeons and other medical personnel will find use for multi-layer amnion dressings in these situations.

In one aspect, embodiments of the present invention encompass methods of manufacturing a multi-layer amnion tissue patch that include obtaining a first amnion tissue layer having an epithelial layer and a basement membrane, where the first tissue layer is treated with a glutaraldehyde exposure process, obtaining a second amnion tissue layer having an epithelial layer and a basement membrane, where the second tissue layer is not treated with a glutaraldehyde exposure process, and contacting the treated first amnion tissue layer with the untreated second amnion tissue layer so as to form the patch, such that the epithelial layers of the first and second amnion tissue layers define first and second opposing outer surfaces of the patch, respectively.

In another aspect, embodiments of the present invention encompass multi-layer amnion tissue patches that include a first amnion tissue layer having an epithelial layer and a basement membrane, and a second amnion tissue layer having an epithelial layer and a basement membrane. The epithelial layers of the first and second tissue layers can define first and second opposing outer surfaces of the patch, respectively. According to some embodiments, the first layer is treated with a glutaraldehyde protocol and the second layer is not treated with a glutaraldehyde protocol.

In still another aspect, embodiments of the present invention encompass methods of manufacturing a multi-layer amnion tissue patch that include obtaining a first amnion sac tissue layer having an amnion layer and a chorion layer, where the first amnion sac tissue layer is treated with a glutaraldehyde exposure process, obtaining a second amnion sac tissue layer having an amnion layer and a chorion layer, where the second amnion sac tissue layer is not treated with a glutaraldehyde exposure process, and contacting the treated first amnion sac tissue layer with the untreated second amnion sac tissue layer so as to form the patch, such that amnion epithelial layers of the first and second amnion sac tissue layers define first and second opposing outer surfaces of the patch, respectively.

In yet another aspect, embodiments of the present invention encompass methods of treating a patient with a multi-layer amnion tissue patch that include obtaining the multi-layer amnion tissue patch, and administering the patch to the patient. The patch may include a first amnion tissue layer having an epithelial layer and a basement membrane, and a second amnion tissue layer having an epithelial layer and a basement membrane. The epithelial layers of the first and second amnion tissue layers can define first and second opposing outer surfaces of the patch, respectively. According to some embodiments, the first amnion layer is glutaraldehyde treated and the second amnion layer is not glutaraldehyde treated.

In still a further aspect, embodiments of the present invention encompass methods of treating a patient with a multi-layer amnion tissue patch, the patch including a first amnion sac tissue layer having an amnion layer and a chorion layer, and a second amnion sac tissue layer having an amnion layer and a chorion layer. According to some embodiments, the first amnion sac tissue layer is treated with a glutaraldehyde exposure process and the second amnion sac tissue layer is not treated with a glutaraldehyde exposure process. According to some embodiments, the first amnion sac tissue layer is contacted with the second amnion sac tissue layer so as to form the patch, such that amnion epithelial layers of the first and second amnion sac tissue layers define first and second opposing outer surfaces of the patch, respectively. Treatment methods further include administering the multi-layer tissue patch to the patient. In some cases, the first amnion tissue sac layer and the second amnion tissue sac layer are each part of a single piece of amnion sac tissue, and the contacting step includes folding the single piece of amnion sac tissue over on itself so that a portion of the first amnion tissue sac layer at least partially overlaps a portion of the second amnion tissue sac layer. In some cases, the first amnion tissue sac layer and the second amnion tissue sac layer are each separate pieces of amnion sac tissue, and the contacting step includes approximating the first and second layers so that a portion of the first amnion tissue sac layer at least partially overlaps a portion of the second amnion tissue sac layer.

In still yet another aspect, embodiments of the present invention encompass a multi-layer amnion tissue patch that includes a first amnion sac tissue layer having an amnion layer and a chorion layer, and a second amnion sac tissue layer having an amnion layer and a chorion layer. In some cases, the first amnion sac tissue layer is treated with a glutaraldehyde exposure process and the second amnion sac tissue layer is not treated with a glutaraldehyde exposure process. In some cases, the first amnion sac tissue layer is contacted with the second amnion sac tissue layer so as to form the patch, such that amnion epithelial layers of the first and second amnion sac tissue layers define first and second opposing outer surfaces of the patch, respectively.

The above described and many other features and attendant advantages of embodiments of the present invention will become apparent and further understood by reference to the following detailed description when considered in conjunction with the accompanying drawings.

BRIEF DESCRIPTION OF THE DRAWINGS

FIG. 4A shows a cross section of a single layer of amnion, and FIG. 4B shows a cross section of a segment of a back-to-back amnion patch, according to embodiments of the present invention.

FIGS. 5A and 5B show aspects of back-to-back amnion dressings according to embodiments of the present invention.

FIGS. 6, 6A, 6B, 6C, and 6D show aspects of back-to-back amnion dressings according to embodiments of the present invention.

DETAILED DESCRIPTION OF THE INVENTION

Figure 1:
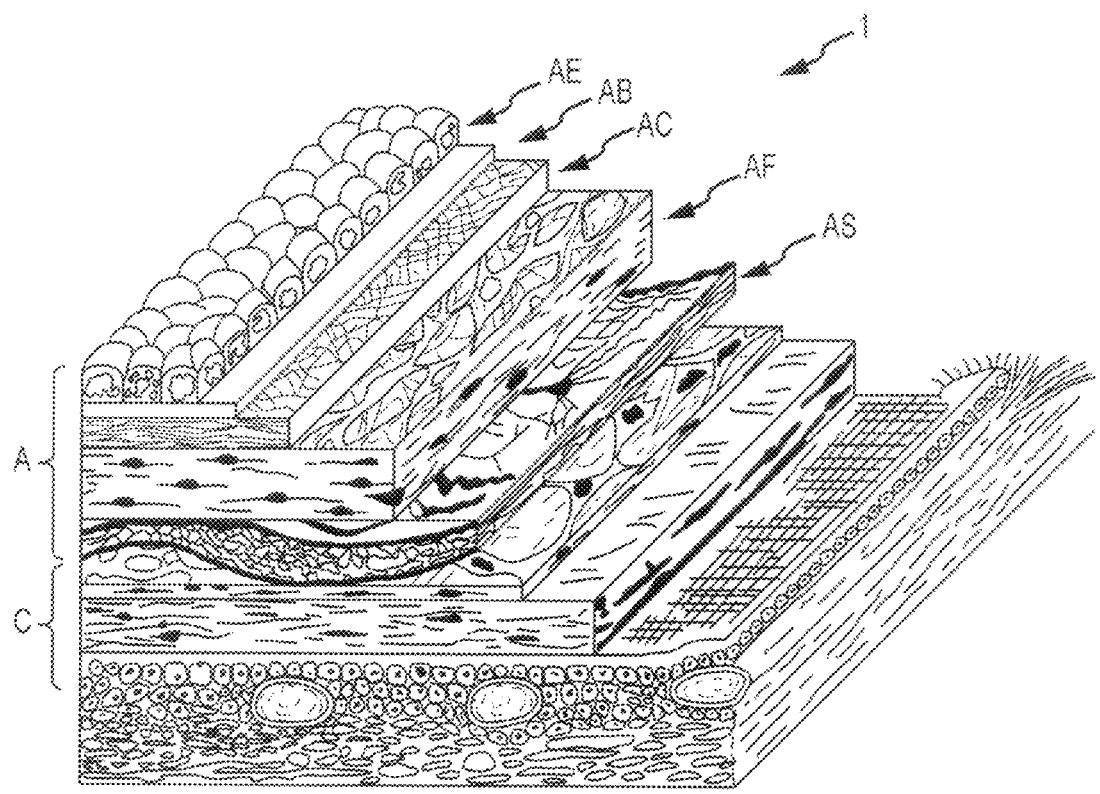
FIG. 1 shows a cross-sectional view of the tissue structure of a segment of the fetal sac according to embodiments of the present invention.

Embodiments of the present invention encompass amniotic dressings or patches formed by folding a portion of amniotic tissue over on itself to form a "back-to-back" amniotic patch having an epithelial layer on both sides of the patch. In some cases, a section of amniotic tissue is folded over and subjected to sufficient pressure to cause fibroblast layers of the amnion to hold the patch together, thus enhancing the mechanical strength of the patch, providing a patch that is easy to handle while maintaining a thin tissue size, and providing a patch having great strength to enable a suture to hold the patch in place at a desired position in the patient. Exemplary back-to-back amnion patches can be used to prevent adhesions in a number of indications involving surgery of the spine, knee, shoulder or child birth, trauma related wounds or injuries, cardiovascular procedures, angiogenesis stimulation, brain or neurological procedures, burn and wound care, ophthalmic procedures, nerve wraps, tendon wraps or in any other procedure where an anti-adhesion barrier is desirable. Amnion tissue is well suited for use for dressings, due to certain immunoprivileged properties and beneficial healing characteristics. Other donor tissues may be used in the manufacture of back-to-back dressings having opposing epithelial outer layers, including intestinal and umbilical cord tissues.

Exemplary amnion processing procedures are described in WO 2009/132186, the content of which is incorporated herein by reference. Methods for producing a single amnion layer may include, for example, obtaining human birth tissue (e.g. amnion, chorion, umbilical cord and placenta), removing the placenta and umbilical cord from the birth tissue, separating the amnion from the chorion, rinsing the amnion with a sterile saline solution, immersing the amnion in a 1% glutaraldehyde solution for a period of up to 15 minutes, rinsing the glutaraldehyde treated amnion in a sterile saline solution. The limited glutaraldehyde treatment provides a lightly cross-linked amnion patch which can be used for implantation within the body. The resulting single layer amnion has an epithelial side and a stromal side. In terms of the original birth tissue amnion, the epithelial surface is on the inner side (facing toward the baby) and the stromal surface is on the outer side (facing toward the mother). Once a single layer amnion tissue is prepared, that amnion layer is then folded over onto itself to provide a double layer patch. When folding, the stromal surfaces face toward each other, with the epithelial surfaces disposed on the exterior. According to some embodiments, the fold is removed by cutting or removing between about 2 mm and 3 mm of the folded edge prior to packaging. Optionally, separate pieces of single amnion layers can be placed together to provide a double layer dressing, with the epithelial surfaces disposed at the exterior surfaces. With regard to the stromal layer, this may also be referred to as the fibroblast layer.

Hence, in some aspects, anti-adhesion wound dressings include one or more of patches made from amnion obtained from human birth tissue. Exemplary amnion patches can be fabricated to provide an epithelial layer on both sides of the patch. In other aspects, embodiments of the present invention are directed to methods of processing human birth tissue to prepare patches made from amniotic tissue, with the patches having an epithelial layer on both sides. In yet another aspect, embodiments of the present invention are directed to methods of using the amniotic patches.

According to some embodiments, the term "amnion" can refer to a thin membrane which forms a closed sac about the embryo and fetus, and contains the amniotic fluid. In some instances, the terms "amnion" and "amniotic sac" may be used interchangeably. The term "stromal" or "stromal side" may refer to the supportive side of the tissue that is fibrous and made up of 4 layers, and may also be referred to as the "smooth side". The term "epithelial side" may refer to the side of the tissue that contains the epithelium (or epithelial cells), which can be a membranous cellular tissue that covers a free surface or lines a tube or cavity of an animal body and serves especially to enclose and protect the other parts of the body. In some instances, the terms "epithelial side", "rough side", and "fetal side" can be used interchangeably. The term "chorion" can refer to the outer most membrane that exists between the mother and the amnion. The term "Wharton's Jelly" can refer to a gelatinous substance located on the exterior of the amnion separating the chorion and amnion. The term "glutaraldehyde" may refer to a compound $C_5H_8O_2$ that contains two aldehyde groups and can be used as a disinfectant and in cross-linking in biological tissues. The term "placenta" can refer to the vascular organ that unites the fetus to the maternal uterus and mediates its metabolic exchanges.

Turning now to the drawings, FIG. 1 illustrates tissue features of a human fetal sac structure 1, including the anatomy of the amnion A and chorion C. As shown here, the amnion layer has several cell layers and has two sides with different cellular components. According to this depiction, the amnion A includes a single layer of ectodermally derived columnar epithelial cells AE adhered to a basement membrane AB. In turn the basement membrane AB includes collagen I, collagen III, collagen IV, laminin, glycosaminoglycans, and fibronectin, and is attached to an underlying layer of connective tissue. The connective tissue includes an acellular compact layer AC of reticular fibers, a fibroblast layer AF, and a spongy layer AS (referred to as Wharton's jelly) which form a network of fine fibrils surrounded by mucus. When the amnion A is separated from the chorion C, a two sided, asymmetrical tissue is produced having an epithelium layer AE with epithelial cells on one side and a fibroblast layer AF on the opposite side. Hence, the separated amnion A includes an epithelial layer AE on one side and a fibroblast layer AF on the opposing side. Between the epithelial and fibroblast layers is a basement membrane AB and a compact layer AC. The fibroblast layer may be considered to include a loose network of reticulum containing fibroblasts. The fibroblast layer also typically includes collagen (e.g. Types I, III, and VI) and glycoproteins (e.g. nidogen, laminin, and fibronectin).

Figure 2:
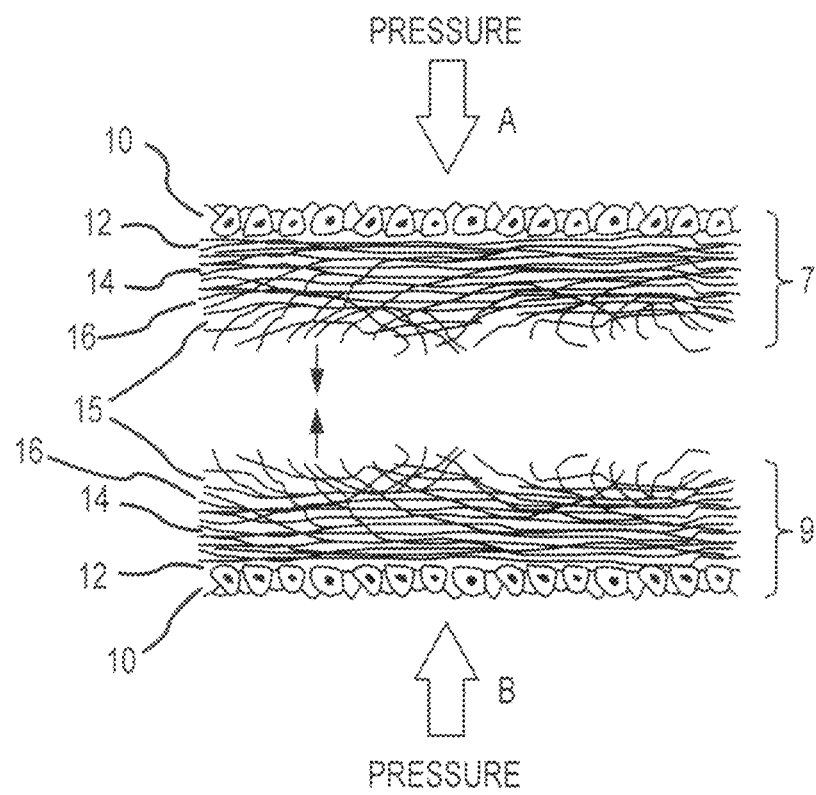
FIG. 2 shows a cross-sectional view of a portion of amnion folded over, and shows the direction in which pressure is applied to the amnion patch, according to embodiments of the present invention.
Figure 3:
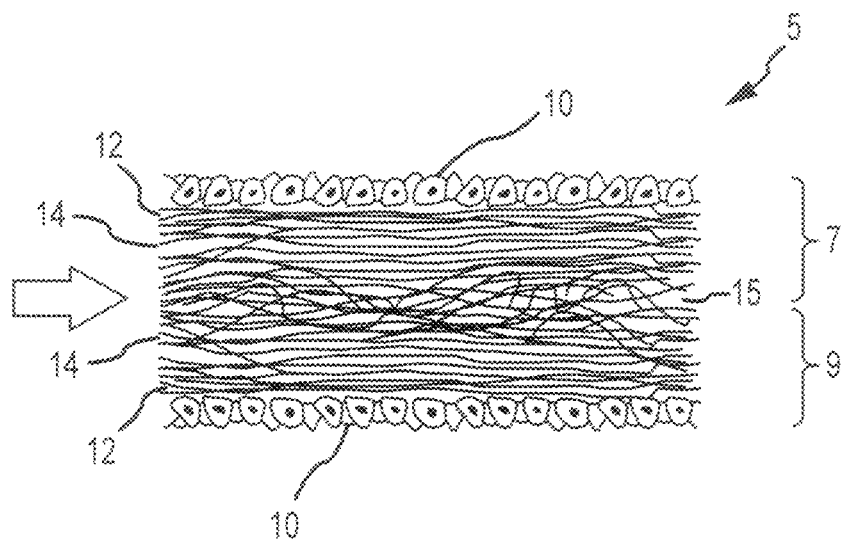
FIG. 3 shows a cross-sectional view of a back-to-back amnion patch, according to embodiments of the present invention.

As shown in FIG. 2, a dressing or patch can be formed by folding a section of amniotic tissue over on itself and pressing it together, or by placing two separate pieces of amnion layer tissue together, such that an epithelial layer 10 is on both the top and bottom outer surfaces of the amnion patch 5, as depicted in FIG. 3. The two sides of the amnion patch 5 also have opposing basement membranes 12, compact layers 14, and fibroblast layers 16. The two fibroblast layers 16 are positioned in proximity with one another, and pressed or adhered to each other in the center of the amnion patch 5 to form a coupled fibroblast region 15. With returning reference to FIG. 2, after an amnion is folded, the fibroblast layer 16 on the top half 7 (e.g. first amnion layer) of the patch faces against the fibroblast layer 16 on the opposing bottom half 9 (e.g. second amnion layer) of the patch. The first and second amnion layers are pressed together as indicated by pressure or force arrows A and B. The fibroblast layers 16 are adhered to each other so as to hold the patch together. The resulting patch can be referred to as a "back-to-back" amnion patch or dressing.

Surprisingly and unexpectedly, the fibroblast layers 16 on the stromal side of the amnion adhere to one another following the pressure treatment, thus holding the first and second amnion layers 7, 9 together. The patch 5 stays together when suspended in saline. The two sides 7,9 may be separated, however, upon application of a physical separation force, such as a peeling force. The patch product can be packaged, terminally sterilized via standard processes known to the skilled artisan, such as gamma irradiation, ethylene oxide, electron beam, and the like, and stored at room temperature. Detailed examples of processes for producing exemplary back-to-back amnion patches are further described elsewhere herein.

FIG. 4A shows a sample of a single amnion layer 40a (20× H & E stained microscope image). FIG. 4B shows a sample of a back-to-back double layer amnion patch 40b having a thickness T (20× H & E stained microscope image). As shown here, the back-to-back amnion patch is generally a mirror image in the horizontal plane in the middle of the tissue. An epithelial layer 10 forms both sides of the outer surface of the patch (e.g. first surface 11, and second surface 13 opposing the first surface). The structure of the back-to-back amnion patch 40b is altered as compared to the native form of amnion 40a in that there are adjacent fibroblast layer fibers and two epithelial sides. The back-to-back amnion patch is often thicker than a single amnion layer. For example, a typical single amnion layer may have a thickness of about 50 microns, and a typical back-to-back amnion patch may have a thickness within a range from about 75 microns to about 200 microns. A back-to-back amnion patch is generally observed to have greater mechanical strength and/or integrity as compared with a single amnion layer. Additionally and surprisingly, a pressed back-to-back amnion patch is generally observed to have greater mechanical strength and/or integrity as compared with two layers of amnion which are adjacent without having been pressed together.

In a typical back-to-back amnion patch, the epithelial layers on both opposing surfaces remain intact, thus providing a barrier to fibrotic encroachment. During a medical procedure, either one of the outer surfaces (e.g. first epithelial layer 10i or second epithelial layer 10ii) of a back-to-back amnion patch can be applied to a patient's dura, so as to prevent or inhibit adhesions. When such placement is performed during surgery, the surgeon is not distracted by focusing on the patch orientation or which side of the patch to apply to the patient. The back-to-back amnion patch does not pose a risk for surgeons that the patch will be improperly or inadequately oriented, because either side can be applied to the surgical area with the expectation of preventing or inhibiting adhesions.

In surgical use during brain or spinal cord procedures, the amniotic tissue or dressing can be oriented with one of the outer epithelial layers positioned away from the dura, and the other opposing outer epithelial layer positioned toward the dura. When oriented in this fashion, the amnion can operate to prevent adhesions. In this way, a back-to-back dressing can prevent or inhibit adhesions of the fill fibrosis to the amnion's epithelial surface. In either orientation, an epithelial layer is in contact with the patient dura.

For example, as shown in FIGS. 5A and 5B, a back-to-back amnion dressing 500 can be placed in the patient in between the cranium 510 and dura mater 520. In the configuration depicted in FIG. 5A, the dressing 500 is oriented so that a first epithelial layer A faces toward the direction of the patient's scalp 530 and the opposing second epithelial layer B faces toward the direction of the patient's cerebral cortex 540. In the configuration depicted in FIG. 5B, the dressing 500 is reversed, so that a first epithelial layer A faces toward the direction of the patient's cerebral cortex 540 and the opposing second epithelial layer B faces toward the direction of the patient's cerebral cortex 540. Embodiments of the present invention also encompass procedures that include the application of a back-to-back amnion dressing to the dura of a patient's spine. In this way, it may not be necessary or desirable to include a marker on the amniotic tissue which distinguishes the epithelial layer from the fibroblast layer, as may be helpful in the case of a single-layer amnion product. The opposing outer epithelial surfaces can help to ensure that the amniotic tissue dressing is properly oriented when placed within the patient, for example to treat a wound, regardless of which side faces toward the dura. Hence, the potential for error in placing the patch on a wound in an incorrect configuration is eliminated.

The opposing outer epithelial surfaces of the back to back patch can also provide beneficial or favorable handling characteristics. For example, in some cases a single layer amnion membrane may tend to roll up readily, whereas a back-to-back patch can present as a flat tissue. Hence, the surgeon or medical personnel can handle and manipulate the back-to-back patch, and the patch maintains a flat or sheet like configuration. Moreover, a back-to-back patch can provide beneficial or favorable suturing characteristics. This can be due to the greater thickness of a typical back-to-back patch, as compared with a typical single layer amnion tissue. The compressed nature and increased density of the compacted back-to-back amnion patch also contributes to these benefits. Due to these features, a back-to-back patch may more adequately hold a suture.

Embodiments of the present invention also encompass methods of processing human birth tissue to prepare patches made from amniotic tissue, with the patches having an epithelial layer on both sides. For example, a human amniotic sac can be collected following a caesarean birth. With returning reference to FIG. 1, a fetal sac typically includes multiple cellular layers which are grouped into tissue referred to as the amnion and the chorion. To prepare a dressing or patch, the amniotic tissue can be separated from the adjoining chorion. In some instances, processing of the multiple cellular layers involves a debridement step, so as to separate the amnion from the chorion. The amnion can be cleaned via a dilute glutaraldehyde solution and sequentially washed to remove the cleaning solution. In some instances the glutaraldehyde rinse operates to fix the amnion layer and render the epithelial cells nonviable, and hence the cells are not capable of metabolic activity or proliferating. In some instances, the amnion layer may be soaked in an ethanol solution, a hydrogen peroxide solution, or both, and subsequently rinsed with saline. Further, the amnion can be cut into sections having specified dimensions.

Any of a variety of cross-linking or decontamination agents can be used to treat the amnion tissue. In additional to glutaraldehyde, other aldehydes such as formaldehyde may be used. In some instances, formalin can be used. These rinsing and cleaning or disinfecting steps can operate to improve the bioburden of the treated tissue, and can also serve to condition the tissue to the desired degree of toughness. In some instances, cross-linking can be achieved with 1-ethyl-3(3-dimethylaminopropyl) carbodimide (EDC), ultraviolet (UV) light, or heat. If the amnion tissue is excessively cross-linked, however, the resulting dressing may exhibit an undesirably high residence time, and thus remain intact within the body for a longer period than intended. Moreover, excessive cross-linking can diminish certain desirable biological characteristics of the dressing. In some cases, if the amnion layers are excessively cross-linked, then following surgery the implanted dressing may trigger or facilitate an encapsulation reaction, whereby the body forms a cyst in association with the dressing. On the other hand, insufficiently cross-linked amnion layers may provoke or facilitate a patient inflammatory response following implantation, or may not provide a residence time sufficient in duration for the intended purpose.

As noted elsewhere herein, certain amnion layer processing steps may include a rinse with glutaraldehyde for a limited amount of time. For example, methods may include rinsing amnion tissue with a 1% glutaraldehyde solution for a period no longer than 15 minutes. Because glutaraldehyde is consumed during the treatment process, much more dilute solutions may not be effective in achieving the desired result. For example, a 0.1% solution may not be sufficiently concentrated to obtain the intended cross-linking or disinfecting objectives. Hence, where lower concentrations are used, it may be desirable to increase the volume of the solution. On the other hand, solutions containing a high concentration of glutaraldehyde may present health or safety issues for those involved with the manufacturing process.

The cross-linking which results from such glutaraldehyde rinses and similar treatments is observed to provide cross-linking at the molecular level which is more significant than cross-linking which may occur at the gross or macroscopic level in response to electron beam sterilization process discussed elsewhere herein.

The rinsing procedures can be performed at or near room temperature (e.g. 22° C.). Processing at higher temperatures, such as body temperature (e.g. 37° C.), may lead to undesirable microbial growth, tissue breakdown in the tissue layers, or both.

To manufacture an exemplary back-to-back amnion patch, a section of amnion can be placed with the epithelial side down on a backing pad. The amnion can then be folded on itself with the epithelial side outward. Slight pressure can be applied to the folded patch, for example in an amount within a range from about 20 psi to about 50 psi, for a sufficient period of time to allow the opposing fibroblast layers to adhere or engage. In some instances, the pressure can be maintained at a value within a range from about 20 psi to about 40 psi. In some case, the application of excessive pressure may result in damage to the dressing tissues.

Without being bound by any particular theory, it is possible that the fibroblast layers on the stromal side of the amnion behave like "Velcro" when adhering together. It is also possible that the amnion fibroblast layer may be damaged as a result of blunt separation from the chorion, thus providing the fibroblast layer with exposed loose fibers that, when pressed together, entangle, intertwine, or intermesh, so that the two fibroblast layers which become engaged or adhered cause the folded or back-to-back amnion patch to be held together. With reference to FIG. 3, it is the fibroblast region 15, or compressed interface or interaction between the two fibroblast layers 16, that provides adherence between the two amnion layers 7, 9. The pressed patch is observed to stay together when suspended in saline, and can be separated upon the application of a physical separation force. Hence, when a section of amniotic tissue is folded over, the fibers of the fibroblast layer of the amnion may become associated or intertwined and hold the patch together with the "Velcro" like effect. The fibroblast layer region 15, which may involve such a biological "Velcro" effect, and can be enhanced by applying mechanical pressure to increase the strength of the patch, provides a patch that is easier to handle while maintaining a thin tissue size, and provide greater strength to enable a suture to hold.

In some instances, the orientation between amnion layers can have an impact on the degree to which the layers adhere to one another. For example, when the material is folded over itself or two fibroblast layers are contacted without mechanical pressure, the material does not separate when placed in solution. Similarly, when the material is cut and the pieces are rotated relative to each other and the fibroblast layers are subsequently contacted without mechanical pressure, the material does not separate when placed in solution. However, when amnion layers are contacted so that the epithelial surfaces of each layer are brought together, the epithelial layers do separate when placed in solution. It is observed that in some instances, when amnion layers are contacted so that epithelial layers are brought together, and the resulting multi-layer assembly is compacted with pressure and subjected to e-beam sterilization, the layers will remain associated when placed in solution.

The thickness of the resulting patch 5 following compression can vary, for example based on the thickness of the amnion layers 7, 9 from which it is produced. In some instances, the patch can have a thickness within a range from about 70 microns to about 200 microns. In some instances, the patch can have a thickness within a range from about 40 microns to about 500 microns. Other exemplary patch thicknesses may be within a range from about 72 to about 197 microns, within a range from about 82 to about 186 microns, within a range from about 75 to about 200 microns, and the like. The thickness of the amnion layers may depend upon certain factors, such as donor variability. It is often observed that younger donors have thicker placental tissues, including thicker amnion layers. In contrast, older donors are often observed to have thinner placental tissues, including thinner amnion layers. The lifestyle or health of the donor may also have an effect on the tissue thickness.

Following the pressure procedure, the product can be packaged, terminally sterilized via electron beam, and stored at room temperature. For example, a dressing product or patch can be packaged in a solution of ethanol or saline. The dressing may in some cases be packaged in a foil packet and sealed. The packet or patch may then be subjected to radiation (e.g. gamma or e-beam), so as to sterilize the package and contents. In many instances, the amnion layers are not dehydrated during processing or prior to packaging. Hence, the processed or packaged dressing typically contains at least partially hydrated amnion layers. In many instances, the amnion layers are not subjected to decellularization techniques during processing or prior to packaging. Hence, the processed or packaged dressing contains non-viable cellularized and intact amnion layers. For example, the epithelial cellular layer, which is responsible for acting as a biological barrier to fibrotic ingrowth, is fully intact after this processing. Additional details producing back to back amnion patches are provided elsewhere herein.

A back-to-back amnion patch can be used to prevent or inhibit adhesions in a number of indications involving surgery of the spine, knee, shoulder or child birth, trauma related wounds or injuries, cardiovascular procedures, angiogenesis stimulation, brain or neurological procedures, burn and wound care, ophthalmic procedures, nerve wraps, tendon wraps or in any other procedure where an anti-adhesion barrier is desirable. Because exemplary back-to-back dressings present outer epithelial layer on both sides of the amnion patch, the dressing can be placed against the patient tissue, wound, or area being treated, without requiring the surgeon or medical personnel to take precautionary measures against inadvertently positioning the dressing in an improper orientation.

A back-to-back amnion patch can be used in virtually any post-operative surgical procedure where anti-scar formation is desired, such as, but not limited to: spine, knee, child birth, shoulder surgery, trauma related cases, cardiovascular procedures, brain/neurological procedures, burn and wound care, nerve wraps and tendon wraps. A back-to-back amnion patch can also be used as a wound cover and a barrier. As a wound cover it can be used where there is injury to a tissue and it needs to be isolated and protected for it to heal and to prevent incorporation into the adjoining tissue in any form and thus to prevent or inhibit adhesions. As a barrier or adhesion preventer or inhibiter, a back-to-back patch can be used where the healing of an injury is across two similar or dissimilar tissues where it is deemed or desired that the tissue or tissues heal isolated from each other even if only one tissue was injured. A back-to-back amnion patch may also be used for dural tears in brain and spinal surgery. A back-to-back amnion patch may also be used for maintaining a space, for example in the knee cap area or anywhere two moving parts need to move freely. In this application, a back-to-back amnion patch can be placed between the two surfaces which are intended to remain separated after any healing phase. A single sided, polar or non-symmetrical amnion has been shown to remain intact at the implant site for at least 8-12 weeks in two different animal models, sheep and dogs. The back to back amnion patch is expected to stay intact for a longer duration.

A back-to-back amnion patch, having epithelial surface on both sides of the tissue, provide a barrier that can prevent or inhibit adhesion to any tissue it is adjacent to. A back-to-back amnion patch also exhibits identical or similar properties on both sides of the patch. In addition, a double layered tissue provides significantly increased mechanical strength, and exhibits an increased ability to hold a suture, while being sufficiently thin for desired surgical applications. A back-to-back amnion dressing may not require a special denotation to the surgeon or medical personnel for identification of which side of the dressing should be placed toward the patient tissue, or otherwise oriented relative to the patient anatomy. This feature can substantially increase the success rate in surgery, because the back-to-back amnion dressing can be placed in the surgical site in either direction while retaining the ability to provide an effective barrier.

As discussed elsewhere herein, back-to-back amnion dressings are well suited for use in a variety of surgical procedures and applications including, without limitation, any situation where the prevention or inhibition of adhesion formation is desired, such as adhesion formation which may otherwise occur during the healing of the target tissue itself or the surrounding tissue. Back-to-back amnion dressings can be used as a nerve wrap, a tendon wrap, an onlay over a bone defect, for the treatment of tarsal tunnel syndrome, and during spinal surgical procedures such as laminectomies, laminotomies, anterior lumbar interbody fusions, and the like. Back-to-back amnion dressings may also be used to treat iliotibial band stenosis, phantom pain associated with amputation (e.g. applied as a nerve wrap), meniscus damage, and the extensor halgus longus tendon.

Figure 6:
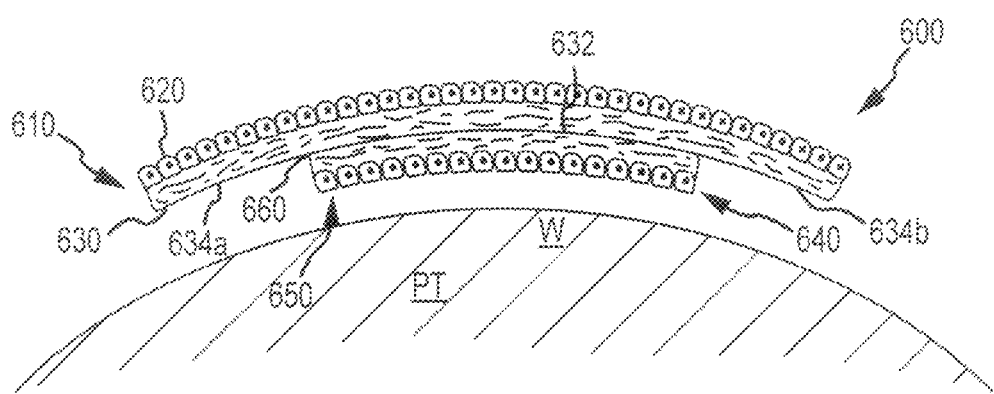

Embodiments of the present invention encompass any of a variety of fabrication constructs that include back-to-back amnion layer features. For example, as shown in FIG. 6, a back-to-back amnion dressing 600 may include a first amnion layer 610 having an epithelial layer 620 and a fibroblast layer 630, and a second amnion layer 640 having an epithelial layer 650 and a fibroblast layer 660. The first fibroblast layer 630 includes a central unexposed portion 632 which is associated or coupled with the second fibroblast layer 660. The first fibroblast layer 630 also includes one or more peripheral exposed portions or tabs 634a, 634b that are not engaged with second fibroblast layer 660. In use, one or more of the fibroblast layer tabs can be positioned against patient tissue PT or against a wound W therein, which may be, for example, at the patient's dura or brain tissue. In this way, the back-to-back dressing can operate similar to a "band-aid". For example, dressing 600 can be placed between the patient's cranium and brain during a craniotomy procedure.

As described elsewhere herein, back-to-back amnion tissue dressings can be used in a variety of surgical applications, including tendon wraps, nerve wraps, and the like. For example as shown in FIGS. 6A to 6C, back-to-back amnion dressings can be wrapped about an anatomical structure of a patient, such as a nerve or tendon. As shown in FIG. 6A, a multi-layer amnion dressing 600a can be wrapped about a patient tendon or nerve. Back-to-back dressing 600a includes a first amnion layer 610a having an epithelial layer 620a and a fibroblast layer 630a, and a second amnion layer 640a having an epithelial layer 650a and a fibroblast layer 660a. The first amnion layer 610a includes a tab portion 612a which is associated or coupled with a tab portion 642a the second amnion layer 640a. Coupling or self-adherence produced via applied pressure between tabs 612a and 642a can provide an annular or cylindrical back-to-back dressing structure, which can be disposed about the patient anatomical structure. Relatedly, as shown in FIG. 6B, a back-to-back dressing 600b can be wrapped about the patient anatomical structure, and secured via a suture 650b where ends or portions of the dressing overlap. Similarly, as shown in FIG. 6C, a back-to-back dressing 600c can be wrapped about the patient anatomical structure, and secured via a suture 650c where ends or portions of the dressing are brought together.

Figure 6D:
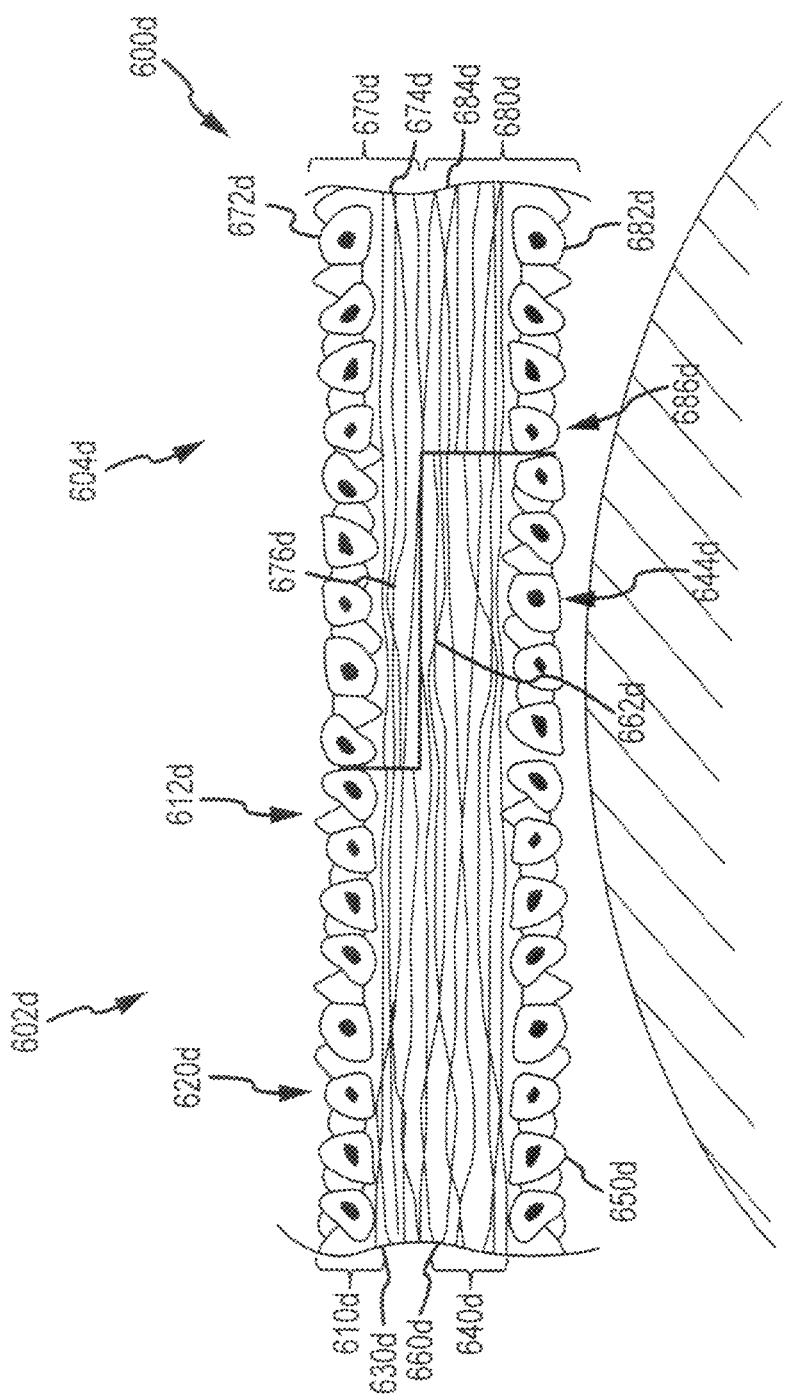

In some instances, it may be possible to manufacture composite amnion dressings containing multiple sheets across an area of tissue. For example, as shown in FIG. 6D, a back-to-back amnion dressing 600d may include a first sheet 602d and a second sheet 604d which can be combined so that they are adjacent one another. First sheet 602d includes a first amnion layer 610d having an epithelial layer 620d and a fibroblast layer 630d, and a second amnion layer 640d having an epithelial layer 650d and a fibroblast layer 660d. First and second amnion layers 610d, 640d are combined in a way such that a tab portion 644d of second amnion layer 640d extends beyond an end portion 612d of first amnion layer 610d. In this way, first sheet 602d presents an unexposed or coupleable area 662d of fibroblast layer 660d. Second sheet 604d includes a first amnion layer 670d having an epithelial layer 672dd and a fibroblast layer 674dd, and a second amnion layer 680d having an epithelial layer 682d and a fibroblast layer 684d. First and second amnion layers 670d, 680d are combined in a way such that a tab portion 676d of first amnion layer 670d extends beyond an end portion 686d of second amnion layer 680d. In this way, second sheet 604d presents an unexposed or coupleable area 675d of fibroblast layer 674d. As shown here, the unexposed or coupleable fibroblast layer areas 662d and 676d can be approximated or brought together, and adhered via application of pressure.

EXAMPLE

In one embodiment, a method for producing a back-to-back amnion patch includes collecting the placenta along with the amniotic sac at the completion of a caesarean section. The collected materials can be shipped overnight on wet ice to a receiving location for processing. The tissue is typically kept refrigerated until it is processed. Using aseptic technique, the amniotic sac, which includes the placenta and fetal sac, is placed on a surface and the amnion is separated from the chorion by blunt dissection. The amnion is placed on a clean surface with the epithelial side down, and the Wharton's jelly is removed using subtle finger pressure and sliding across the stromal side of the tissue. After the Wharton's jelly is removed, the amnion is washed with three sequential volumes of 500 ml of 0.9% saline. The amnion is then soaked in a 1% glutaraldehyde solution for 15 minutes on a horizontal rotator. Following the glutaraldehyde soak, the amnion is rinsed with three sequential volumes of 500 ml of 0.9% saline. The washed amnion can be spread out and cut to a selected size. The amnion may be cut to any desired size or shape (i.e. square or horizontal) to obtain the desired size of the back to back amnion patch, for example after the amnion is folded over (e.g. folded over in half). For example, the amnion may be cut in squares ranging in size from 2 cm by 2 cm to as large as 11 cm by 11 cm. Alternatively, the amnion may be cut in horizontal sizes ranging from 2 cm by 4 cm (which can form a 2 cm by 2 cm square patch when folded over) to 11 cm by 22 cm (which can form a 11 cm square patch). The invention is not limited in this regard, and any desired size and shape may be used.

The cut amnion can be placed on a backing material with the epithelial side of the amnion contacting the backing material. The backing material may be any appropriate material for use with amniotic tissue, including materials such as non-woven Delstar, cotton gauze with sealed edges or hydrophilic webbing. With the amnion on the backing material, the amnion can be folded over in half making sure the amnion does not separate from the backing material. When folded, the opposing stromal sides of the section of amnion are in contact with each other. The folded amnion with backing material can be placed in a Kapak pouch with care to keep the amnion folded inside the backing material. The Kapak pouch can be placed between two hard plastic plates and squeezed gently using hand pressure to remove excess air. Care can be taken to avoid squeezing out the moisture retained in the backing material to keep the tissue moist. The pouch can be sealed using a heat sealer. The sealed Kapak pouch can be placed in a Chevron bag and again placed between two hard plastic plates and squeezed gently using hand pressure to remove excess air. After the air is removed, the bag can be heat sealed. The bagged amnion can then be placed on a press and subjected to between 20-200 psi of pressure while being maintained at 4-8° C. The pressure is maintained on the bagged amnion for a sufficient time to allow the opposing fibroblast layers to adhere or couple together. In one embodiment, the pressure is maintained overnight (i.e. for approximately 12 hours). At the completion of the pressing cycle, the bagged amnion is removed from the press and sterilized via electron beam sterilization at 25 kGy.

EXAMPLE

Preparation of a back-to-back amnion dressing typically involves aseptically placing donor material onto a sterile field. For example, the donor tissue can be aseptically placed on a sterile board or in a sterile container. The chorion/amnion sac can be identified, for example, as the opaque-to-clear sac that is attached to the placenta. The chorion/amnion can be separated from the placenta by blunt dissection. The placental can be discarded. The chorion and Wharton's jelly can be removed from the amnion by blunt dissection. A sterile container is filled with approximately 400 mL of 0.9% saline solution. The amnion is dipped in the solution and blood clots, residual chorion, and Wharton's jelly, are removed.

In a further amnion rinsing step, a new sterile bowl is filled with approximately 400 mL of 0.9% saline solution. The amnion is placed into the saline solution and the bowl is placed on an orbital shaker. The RPM setting of the shaker is adjusted as appropriate to create a gentle roll of solution over the amnion. Agitation is performed for 2 minutes. To remove any remaining Wharton's jelly, these steps may be performed repeatedly, for example for one more cycle for a total of two rinses.

Subsequently, a glutaraldehyde treatment of the amnion can be performed which includes placing a sterile stainless steel tray or pan onto an orbital shaker, filling the tray with 500 mL of 1% glutaraldehyde solution. The amnion is placed in the glutaraldehyde solution, and the RPM setting on the shaker is adjusted as appropriate to create a gentle roll of the solution over the amnion. The amnion is left in the solution for 14±1 minutes. As tissue is rotating in the solution, it may be helpful to ensure the tissue remains spread out. According to some embodiments, if the tissue remains in this glutaraldehyde longer than 15 minutes, it may be desirable to discard the tissue. Excessive cross-linking treatments can toughen or tan the tissue to such a degree that the tissue is no longer suitable for its intended purpose. In some cases, glutaraldehyde treatments can be carried out at a temperature of about 22° C. Typically, the treated amnion tissue persists within the body for the duration of the healing phase.

The tissue may be subjected to additional glutaraldehyde treatments. A new sterile stainless steel tray or pan is filled with 1000 mL of 0.9% saline solution, the amnion is placed into the saline solution, and the tray or pan is placed on an orbital shaker. The RPM setting on the shaker is adjusted as appropriate to create a gentle roll of solution over the amnion. Agitation is performed for 3 minutes. As tissue is rotating in the solution, it may be helpful to ensure the tissue remains spread out. Such additional glutaraldehyde treatments can be performed repeatedly, for example for two more cycles for a total of three such rinses.

Upon ensuring that all Wharton's jelly is removed, the amnion can be placed on the cutting board with the epithelial side facing up and the stromal side facing down and a corresponding appropriately sized backing material is selected and soaked in a 0.9% saline solution. The backing material is then placed on the epithelial side of the tissue, and the tissue is cut along the edge of the backing material. The backing material/tissue is lifted and turned over onto the cutting board so that the backing material is now on the bottom and amnion is on the top (i.e. the stromal side is facing upward).

The folded or multi-layered amnion tissue is placed in an appropriately sized container, such as a Kapak pouch. 1 cc of 0.9% saline solution is placed in the Kapak pouch. The Kapak pouch containing the backing material, tissue, and solution is placed in appropriately sized chevron pouch. It may be helpful to ensure that excess or undesirable air is removed from the chevron pouch prior to creating a seal at approximately the top of the chevron pouch, for example with a heat sealing device.

Figure 7:
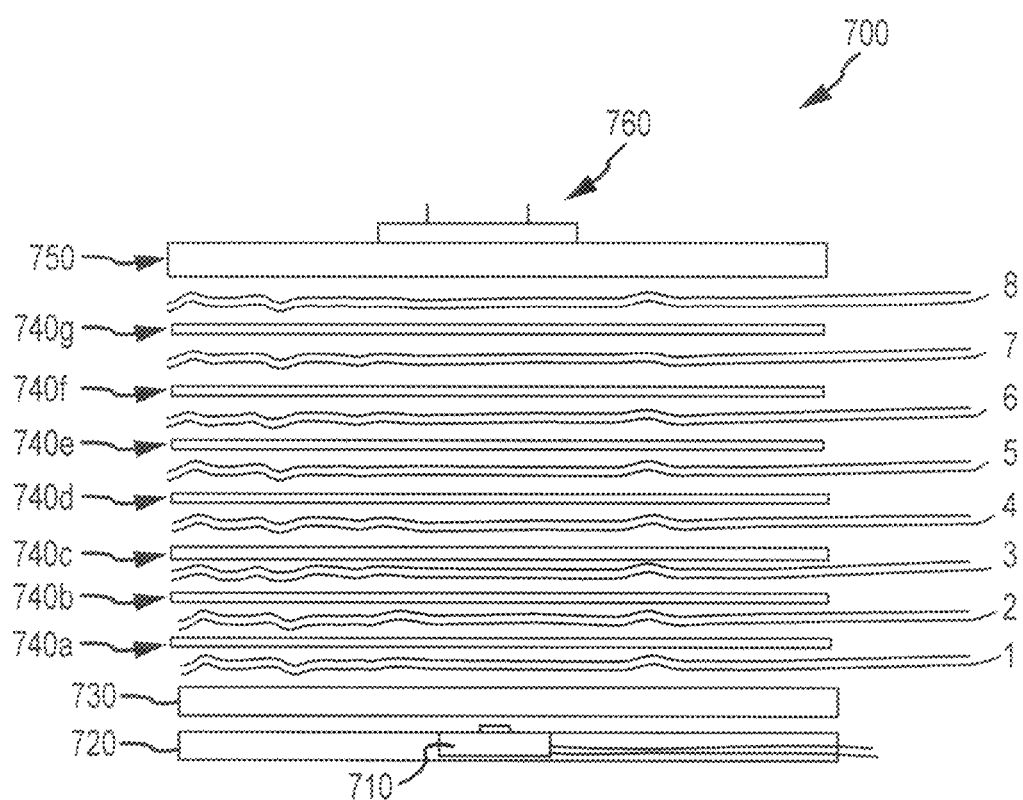
FIGS. 7, 7A, and 7B illustrates aspects of back-to-back amnion patch production techniques, according to embodiments of the present invention.

One or more chevron pouches can be placed on a tissue press mechanism 700 as shown in FIG. 7. Press mechanism 700 may include a load cell 710 embedded in a support plate 720, a base plate 730, any number of pressure leveling plates 740a to 740g, a top plate 750, and a pressure foot 760. Chevron pouches containing the amnion tissue compositions can be placed in the press mechanism, for example between base plate 730 and a leveling plate, between individual leveling plates (e.g. between 740a and 740b), or between a leveling plate and the top plate 750. In some cases, where there are leveling plates, a tissue sample can be placed between the base plate and the top plate. As shown here, pouches 1-8 are placed in the press mechanism.

In operation, the applied pressure can be identified by the pressure cell. The tissue press can be adjusted to depress the pressure foot to achieve any desired amount of pressure. For example, the press mechanism 700 may be used to apply a pressure of 44 psi to the chevron pouches, and consequently, to the tissue samples. Following application of pressure for an indicated amount of time (e.g. 10-15 minutes), the sealed chevron pouches can be removed from the press. The Kapak pouches can then be removed from the chevron pouches. The sealed packages can be stored in a refrigerator at a temperature between about 1° C. and about 10° C. The package can also be sterilized with an E-beam sterilization mechanism.

EXAMPLE

The biomechanical characteristics of exemplary back-to-back amnion dressings were evaluated. The tensile strength of exemplary dressings were evaluated, to determine the effect of pressure/time on the tensile strength of back-to-back dressing configurations, and to compare them to single layered amnion configurations. Various back-to-back dressing configurations, including dressings that include rotated layers of amniotic tissue, were evaluated.

For example, a back-to-back amnion dressing was evaluated for tensile strength using an Instron system. Dressing samples having a size of 5×5 cm size were subjected to pressures of ~20, 25, 40, 50, and 56 psi overnight for 18-24 hours at sub-ambient conditions using a tissue press design such as that shown in FIG. 7. A 5×5 cm size back-to-back dressing can be prepared from a 5 cm×10 cm rectangles of single-layer amnion. At this point the amnion is on top off a layer of backing material and the amnion is orientated with the stromal side exposed and the epithelial side against the backing material. The 5×10 rectangle is then folded with the folded amnion between two layers of backing material. For one sample, the 5×10 cm piece was cut into two 5×5 cm pieces and then one piece was rotated 90 degrees and the flipped over on top off the other piece with the epithelial side away from each other. Saline solution was added to the package to keep the tissue wet. Each sample was packaged in a 4"×6" Kapak pouch and heat sealed and then placed in a 6"×16" Chevron pouch and heat sealed. At each package care was taken to remove excess air before sealing. The packages were then subjected to the pressures prescribed. After pressurizing the packages were terminally sterilized using electron beam at 25 kGy (BeamOne, Commerce City, Colo.).

The pressure applied can be identified by placing a pressure cell at the base of the tissue press. In some examples, the samples were stacked with ⅛" hard plastic pressure leveling plates between each sample and a ⅜" delrin plate below and at the top of the stack to distribute and level off the pressure applied through the stack of samples. Tissue from multiple donors was used to gain an understanding of the donor to donor variability.

The pressure each tissue press imposed on the samples is tabulated in Table 1. The last column was evaluated and the pressures grouped to differentiate the samples into pressure ranges. The samples that observed pressure between 19 psi and 24 psi were grouped into a medium pressure of 22 psi. The samples that experienced pressure between 27 psi and 29 psi were grouped into the medium pressure of 28 psi. The samples that experienced pressure between 36 psi and 54 psi were grouped into the medium pressure of 45 psi. The final group of samples that experienced pressure between 45 psi to 57 psi were grouped into the medium pressure of 52 psi.

TABLE 1

| | Pressure (psi) | | |
|---|---|---|---|
| Tissue Press | High | Low | AVG |
| 3 | 24 | 19 | 21 |
| 4 | 24 | 20 | 22 |
| 2 | 27 | 29 | 28 |
| 4 | 50 | 36 | 43 |
| 2 | 51 | 39 | 45 |
| 3 | 54 | 37 | 46 |
| 4 | 55 | 45 | 50 |
| 2 | 57 | 50 | 53 |

Figure 7A:
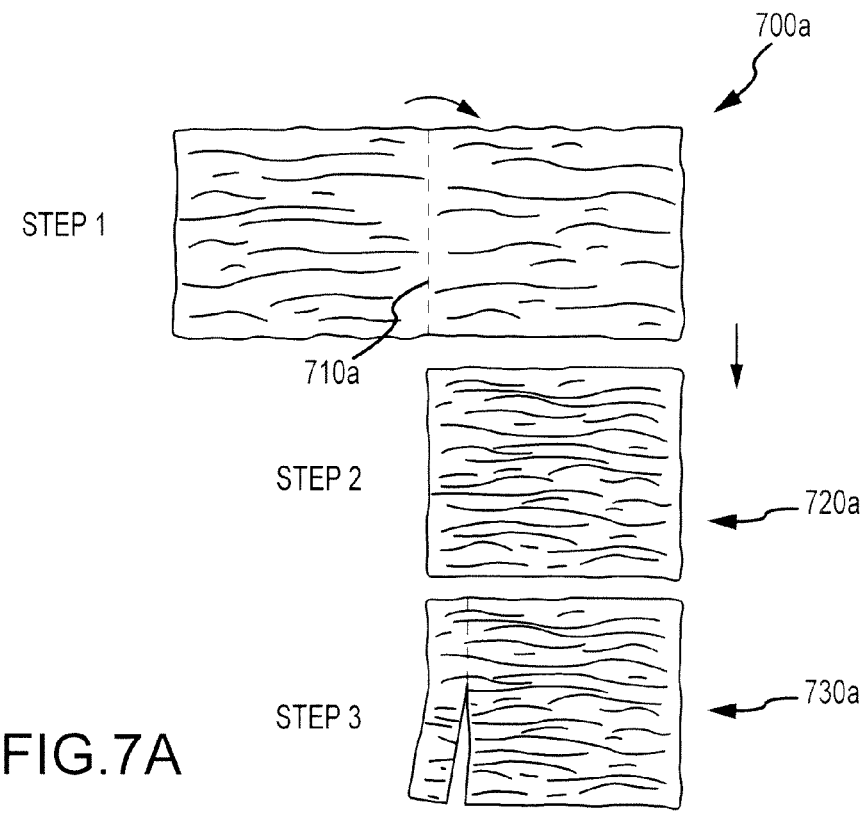
Figure 7B:
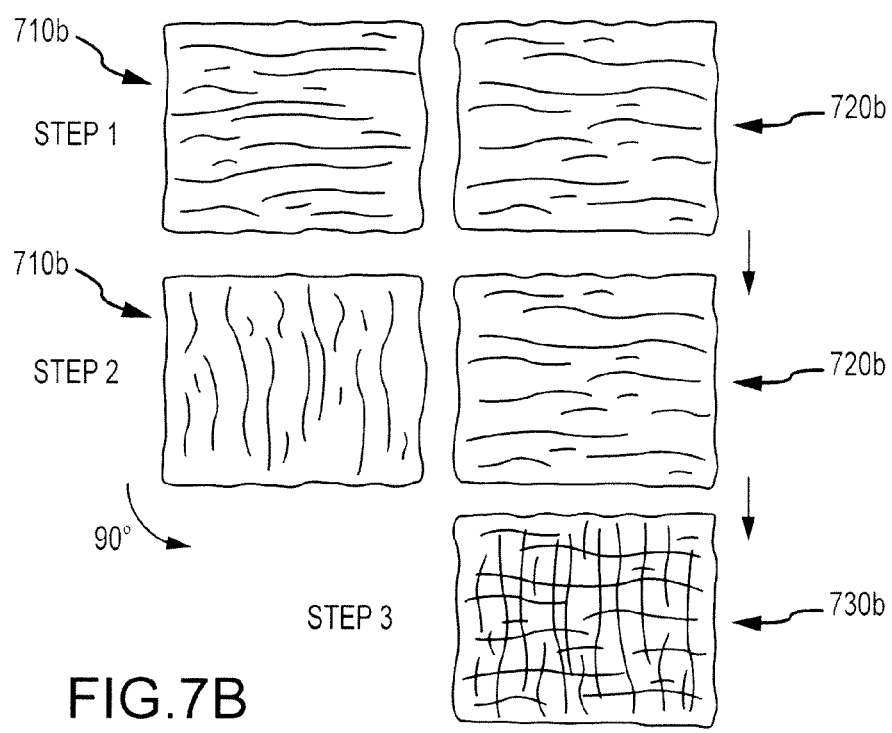

FIGS. 7A and 7B illustrate certain aspects of dressings which were tested. As shown in FIG. 7A, a single layer amnion dressing 700a can be folded along a fold line 710a, so as to provide a back-to-back amnion dressing 720a (double-sided, or DS) having a fold along the left side of the patch. In some cases, the fold can be removed or cut away from the patch, so as to provide a back-to-back amnion dressing 730a (double-sided, or DS) that does not have a fold. As shown in the lower row of FIG. 7A, the fold is in the process of being severed or removed. For example, the fold can be removed prior to placing the patch in a package. Relatedly, as shown in FIG. 7B, a single layer amnion dressing can be cut or separated into two distinct single layer amnion dressing pieces 710b and 720b. One of the single layer amnion pieces can be rotated relative to or angularly offset from the other. As shown here, amnion piece 710b is rotated 90 degrees. Amnion pieces 710b and 720b are then approximated and pressed together, so as to provide a back-to-back amnion dressing 730b (double-sided, or DS).

The tensile strength of twelve samples was measured. For back-to-back amnion dressing samples, each sample was cut in half to fit on the clamps of the tensile testing system and both halves tested. For single layer amnion dressings, a total of 4 tests were completed. The rotated back-to-back dressing was cut into two pieces and both halves tested. Table 2 presents the summarized results.

TABLE 2

| | DS (folded) | | | | DS (rotate 90 degrees) 38 psi [N/mm2] | Single layer na [N/mm2] |
|---|---|---|---|---|---|---|
| | 22 psi [N/mm2] | 28 psi [N/mm2] | 45 psi [N/mm2] | 51 psi [N/mm2] | | |
| n | 3 | 4 | 6 | 4 | 2 | 7 |
| Average | 17.7 | 14.2 | 11.0 | 15.0 | 20.8 | 7.7 |
| Standard Dev. | 3.9 | 3.9 | 3.3 | 3.0 | 2.8 | 3.1 |

According to the embodiments tested, when the back-to-back folded dressing is pressurized at ~22 psi for 18 hours, the tensile strength is observed to be more than twice as strong as the single layer (17.7 N/mm$^2$ vs. 7.7 N/mm$^2$) and is statistically different (P=0.002). Applying higher pressure for 18 hours appears to negatively affect the tensile strength of the tissue. The highest tensile strength was obtained at the lowest pressure applied for 18 hours. The samples pressurized above 50 psi appear more brittle when handling. An earlier experiment that had no pressure monitoring showed that at very high pressure the samples were brittle and suturing caused a running tear and the suture itself cut through the tissue with ease. Without being bound by any particular theory, it is believe that one explanation may be that at higher pressures the tissue structure may be adversely altered. In some instances it has been observed that the thickness of the tissue is naturally variable with the thickness of the amnion dependent on the geographical location within a single donor. For example, the tissue close to the placenta is much thicker than the amnion at the opposite end of the fetal sac. Two hematoxylin and eosin (H&E stain) histology light microscopy pictures of placental tissue shown in FIG. 8A (20×, close to placenta) and FIG. 8B (20×, opposite side of fetal sac) illustrate this feature.

Figure 8A:
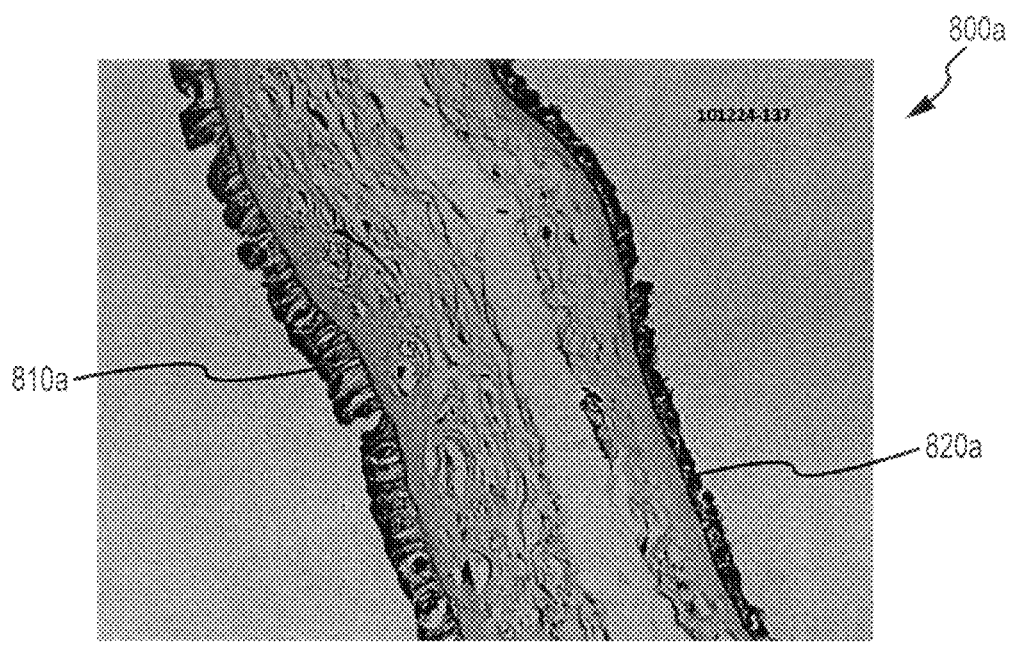
FIGS. 8A, 8B, 8C, and 8D show aspects of back-to-back amnion dressings according to embodiments of the present invention.
Figure 8B:
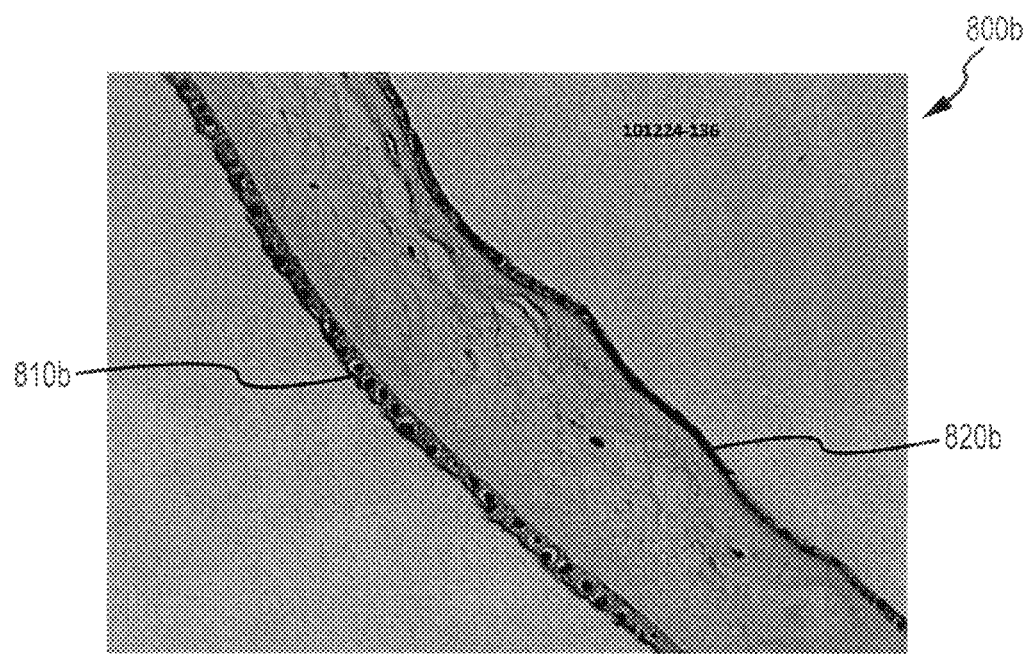

FIG. 8A shows a sample of amnion 800a folded onto itself. The epithelial layer 810a on the left side of this image is from tissue closer to the placenta, whereas the epithelial layer 820a on the right side of this image is from tissue further from the placenta. FIG. 8B is an image of another back-to-back dressing 800b prepared from tissue from the same donor depicted in FIG. 8A, however the tissue shown in FIG. 8B is taken from a sample located further away from the placenta, and the tissue shown in FIG. 8A is taken from a sample located more closely to the placenta. The tissue 810b at the left side of FIG. 8B is derived from a location closer to the placenta, and the tissue 820b at the right side of FIG. 8B is derived from a location further away from the placenta. The relative thickness of the tissue is evident in these two figures. The left-most layer 810a in FIG. 8A (closer to placenta) is about six times thicker than the right most layer 820b in FIG. 8B (further from the placenta).

Figure 8C:
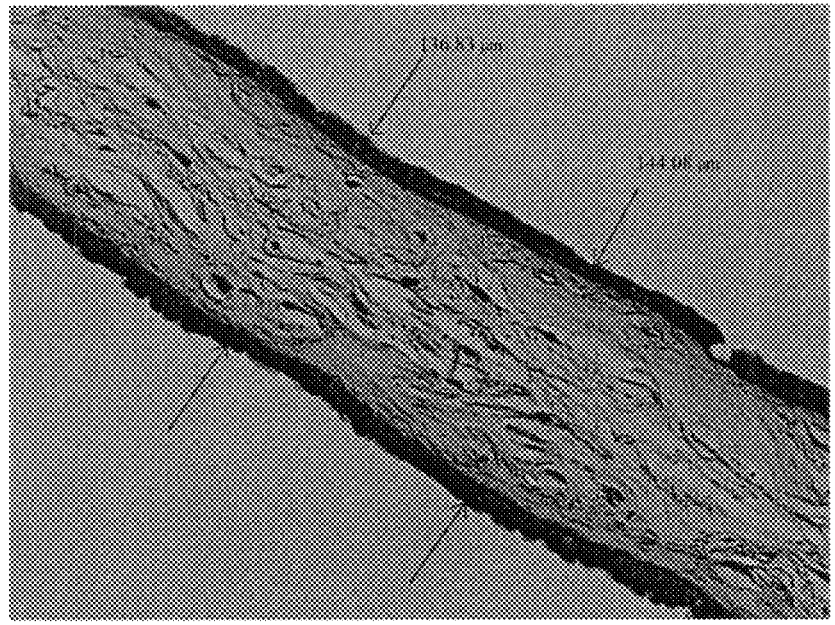
Figure 8D:
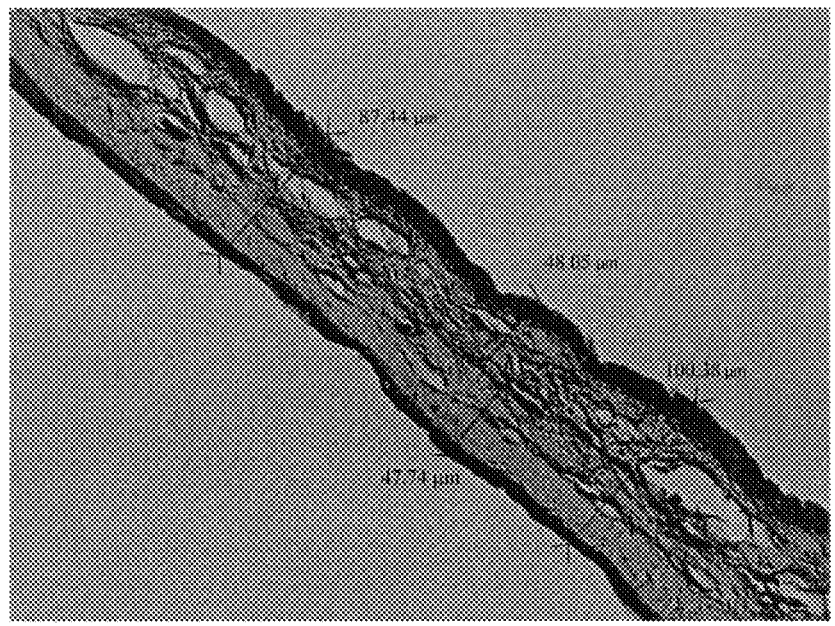

As shown in FIG. 8C, an exemplary back-to-back dressing can have a thickness of about 136.83 microns at one location, and a thickness of about 144.08 microns at another location. Relatedly, as shown in FIG. 8D, an exemplary back-to-back dressing can have a thickness of about 87.44 microns at on location, and a thickness of about 100.38 microns at another location. As depicted here, the thickness of a first amnion layer is about 48.05 microns and the thickness of a second amnion layer is about 47.74 microns.

It was unexpectedly and surprisingly observed that rotating layers of amnion relative to each other enhanced certain characteristics of the multi-layer amnion dressing. For example, rotating the two layers of amnion 90 degrees to each other is observed to improve the tensile strength of the tissue. An exemplary sample tested generated an average tensile strength of 20.8+/−2.8 N/mm$^2$. Without being bound by any particular theory, the increase of tensile strength when rotating the two layers indicates that there may be unorganized orientation to the tissue that has not been published in the literature to date.

EXAMPLE

The tensile and suture pullout strength of multi-layer amnion dressings manufactured at two pressures (80 lbs and 150 lbs) with incremental time lapse were evaluated. Multi-layer samples were prepared using the manufacturing methods described herein. 4×4 cm size samples were prepared, packaged in 4×6 Kapak pouches, heat sealed, placed in a 6×16 Chevron pouch, and heat sealed. At each packaging step, care was taken to remove excess air before sealing. After pressurizing, the packages were terminally sterilized using electron beam at 25 kGy (BeamOne, Commerce City, Colo.). Multi-layer amnion dressings in the 5 cm×5 cm size were subjected to pressures of 20 psi and 38 psi for 0, 1, 15, 60, 120 minutes at ambient conditions using the tissue press techniques described elsewhere herein. Samples were loaded on to the tissue press and pressed, 3 samples at each time.

All samples were evaluated for tensile strength and suture pullout strength. In preparation for testing, the dressings were rinsed with phosphate buffered saline, patted dry to remove excess moisture, and then sectioned into two (2) 25×50 mm strips. The 2nd strip from each dressing was labeled and set aside for the suture testing. Once cut to size, the actuator height was adjusted to maintain a 15 mm active length between grips with 17.5 mm of tissue engaging each grip end. Each specimen was centered between the superior and inferior gripping fixtures with a strip of emery cloth on its ends for improved grip and less risk to slippage, and then grips were tightened to secure the specimen. A tensile load was applied to each specimen using a servo-hydraulic test machine at a rate of 10 mm/min. under displacement control until failure was achieved. Failure was designated as a rapid loss in tensile force and/or compromised tissue.

Using 4.0 prolene suture material, pullout tests were performed on the 2nd half of the matching amniotic membrane tissue pairs from static tension procedure to determine the tissue resistance to suture pullout. The tissue grafts were rinsed with phosphate buffered saline, patted dry to remove excess moisture. The suture was passed through a hole 1 cm down from the top edge and 1.25 cm from the lateral edge in all the tissue and a whip stitch suture style was used to secure the suture to the tissue, with the end of the suture free for fixturing to the gripping fixtures of the test machine. The non-sutured edge of the tissue was gripped 1 cm and the free suture end tied to the superior gripping fixture. A tensile load was applied to each specimen using a servo-hydraulic test machine at a rate of 10 mm/min. under displacement control until failure was achieved. Failure was designated as a rapid loss in tensile force and/or compromised tissue or suture.

Multi-layer amnion dressings were processed as described herein and samples were subjected to a specific pressure using a calibrated pressure gauge. Each sample was then processed through a H & E staining procedure and histology images generated. Nikon Imaging Software was used to obtain cross-sectional measurements. 5 measurements were made and then the widest, the thinnest and a medium thickness measurement were recorded for each sample. These measurements were then evaluated using Minitab Statistical Analysis tools to evaluate the data. It was observed that the tensile strength of a back-to-back amnion dressing doubles in strength with just 2 minutes of 20 psi of pressure, and almost triples when 38 psi of pressure are applied for 1 minute as compared to back-to-back amnion dressings that have not been pressurized. For the samples exposed to 20 psi of pressure the tensile strength does not increase above the initial increase until more than 60 minutes of pressurized time whereas, the samples exposed to 38 psi of pressure show a decrease in tensile strength with increased time at the higher pressure.

Table 3 shows the tensile strength of back-to-back amnion dressing pressurized at 20 psi and 38 psi over time.

TABLE 3

| Tensile Strength [N/mm$^2$] | | |
| --- | --- | --- |
| Time (min) | 20 psi | 38 psi |
| 0 | 6.6 | 6.6 |
| 1.5 | 12.6 | 17.0 |

TABLE 3-continued

| Tensile Strength [N/mm$^2$] | | |
| --- | --- | --- |
| Time (min) | 20 psi | 38 psi |
| 15 | 9.4 | 15.8 |
| 120 | 18.2 | 14.0 |

Table 4 shows the ultimate load required for pullout of a 4.0 suture in a back-to-back amnion dressing.

TABLE 4

| Ultimate Load [N] | | |
| --- | --- | --- |
| Time (min) | 20 psi | 38 psi |
| 0 | 0.50 | 0.50 |
| 1.5 | 0.62 | 0.70 |
| 15 | 0.41 | 0.54 |
| 120 | 0.58 | 0.61 |

Table 5 shows a summary of data recorded from histology H & E images from each of the samples. One donor was used for the measurement experiment to reduce the variability of donor to donor and concentrate on the effect of pressure and time on amnion. The thickness of the double sided amniotic tissue was measured on H & E histology images using Nikon's Imaging System NIS-Elements BR 3.1 program. The location of the measurement on the image were random and an attempt to include the widest and the thinnest sections in the values generated. Table 5 also provides statistical data on thickness of a back-to-back amnion dressing vs. time and pressure.

TABLE 5

| Sample ID [Pressure Time] | Average Thickness [microns] | n |
| --- | --- | --- |
| 0 psi 0 min | 162.45 | 18 |
| 20 psi 5 min | 134.43 | 12 |
| 20 psi 20 min | 131.34 | 6 |
| 38 psi 5 min | 124.49 | 12 |
| 38 psi 20 min | 90.73 | 6 |
| 50 psi 5 min | 140.67 | 12 |
| 50 psi 20 min | 114.63 | 6 |

Analysis of the data shows that the thickness of back-to-back amnion dressing can be significantly altered as a result of the pressure applied thereto. Thickness can also be dependent on how long the pressure is applied to the sample.

It is observed that pressure applied for an elapsed amount of time is helpful to induce the formation of a double layer amnion tissue dressing, with the stromal sides of the amnion layers forming a bound surface between the amnion layers. In instances where tissue is pressed together with 20 psi of pressure, the ultimate tensile strength could not be identified as the slope of the curve of pressure vs. time at 120 minutes was still positive. In contrast, for the tissue pressed at 38 psi of pressure, a peak was observed within 15 minutes and trended downward at 60 minutes and flat between 60 and 120 minutes. Applying a moderately higher pressure for a short amount of time appears to provide an effective protocol for processing tissue. For example, the application of 38 psi of pressure for 15 minutes or less may provide a suitable technique for the production of a back-to-back amnion dressing. Results from suture pullout strength tests suggest that application of 38 psi for 15 minutes or less is better than the application of no pressure. The thickness of the final product was shown to change during the pressing of the double layered amnion and it is visibly apparent that the change in the amnion is in the compaction of the stromal fibrous material. The epithelial cells appear to be intact even at the highest pressure of 50 psi for 20 minutes. There is a visible increase in the density of fibers at the middle of the folded amnion where the two layers of the stromal sides meet.

Figure 10A:
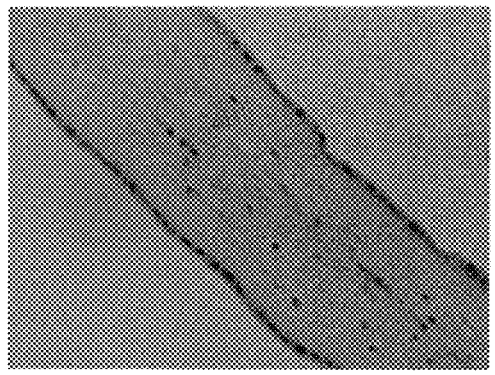
FIGS. 10A and 10B illustrate compression characteristics of exemplary back-to-back tissue patches according to embodiments of the present invention.
Figure 10B:
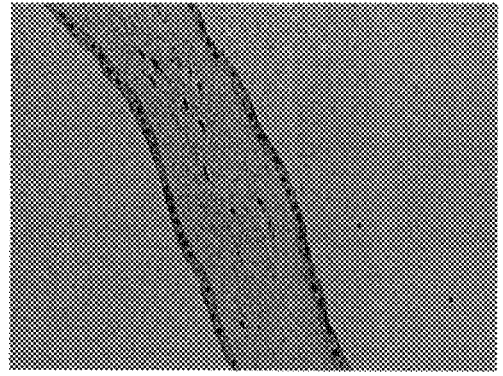

FIGS. 10A-13B illustrate exemplary changes in thickness or compaction levels of stromal fibrous material in response to the application of pressure. For example, FIG. 10A shows an exemplary back-to-back amnion dressing 10000 having a thickness of about 165 microns, in the absence of an applied compression pressure. FIG. 10B shows dressing 10000 after a compression pressure of 20 psi for a duration of five minutes. As depicted here, the compacted dressing was subsequently observed to have a thickness of about 105 microns.

Figure 11A:
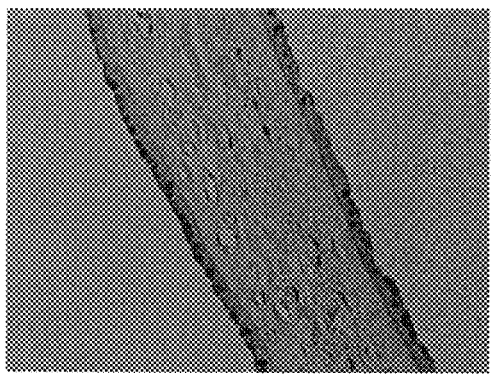
FIGS. 11A and 11B illustrate compression characteristics of exemplary back-to-back tissue patches according to embodiments of the present invention.
Figure 11B:
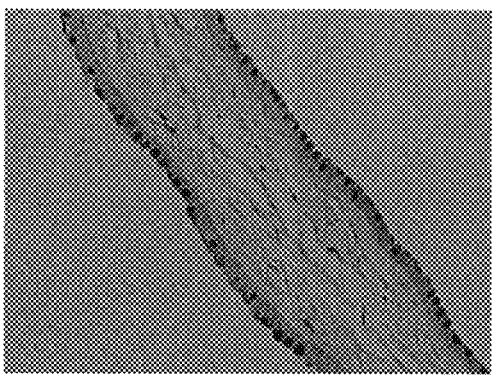

FIG. 11A shows an exemplary back-to-back amnion dressing 11000 having a thickness of about 155 microns, in response to an applied compression pressure of 20 psi for a duration of 5 minutes. FIG. 11B shows dressing 11000 after a compression pressure of 20 psi lbs for a duration of 20 minutes. As depicted here, the further compacted dressing was subsequently observed to have a thickness of about 130 microns.

Figure 12A:
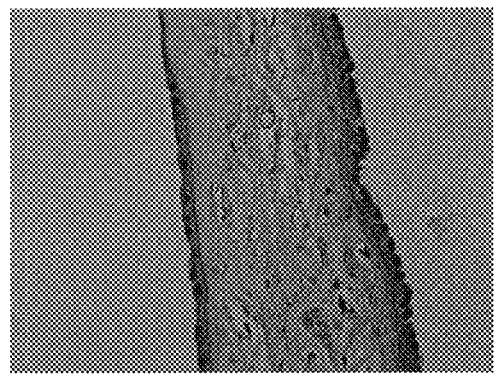
FIGS. 12A and 12B illustrate compression characteristics of exemplary back-to-back tissue patches according to embodiments of the present invention.
Figure 12B:
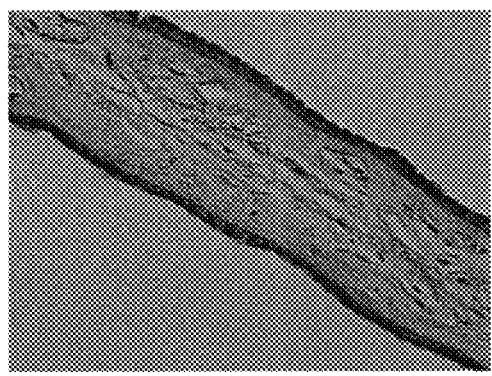

FIG. 12A shows an exemplary back-to-back amnion dressing 12000 having a thickness of about 185 microns, in the absence of an applied compression pressure. FIG. 12B shows dressing 12000 after a compression pressure of 38 psi for a duration of five minutes. As depicted here, the compacted dressing was subsequently observed to have a thickness of about 142 microns.

Figure 13A:
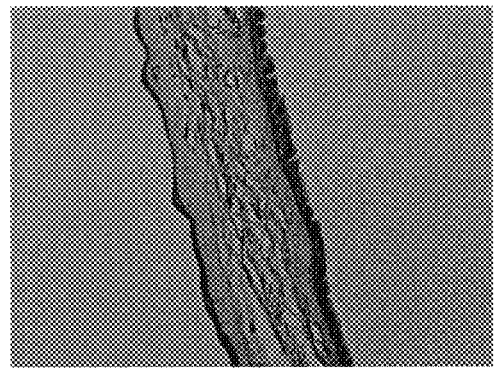
FIGS. 13A and 13B illustrate compression characteristics of exemplary back-to-back tissue patches according to embodiments of the present invention.
Figure 13B:
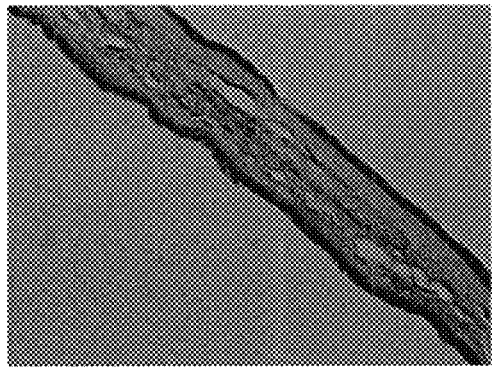

FIG. 13A shows an exemplary back-to-back amnion dressing 13000 having a thickness of about 116 microns, in response to an applied compression pressure of 38 psi for a duration of 5 minutes. FIG. 13B shows dressing 13000 after a compression pressure of 38 psi for a duration of 20 minutes. As depicted here, the further compacted dressing was subsequently observed to have a thickness of about 89 microns.

Figure 9:
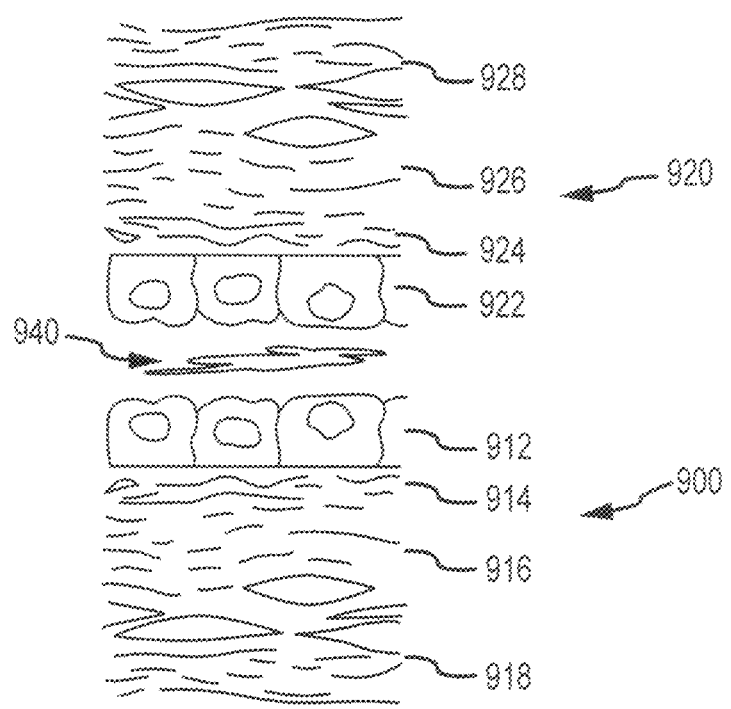
FIG. 9 depicts a cross-sectional view of a back-to-back amnion patch, according to embodiments of the present invention.

Embodiments of the present invention also encompass multi-layer amnion tissue constructions that present outer stromal surfaces on opposing sides of the dressing. For example, as shown in FIG. 9, a multi-layer amnion dressing 900 may include a first amnion layer 910 having an epithelial layer 912, a basement membrane 914, a compact layer 916, and a fibroblast layer 918. Amnion dressing 900 may also include a second amnion layer 920 having an epithelial layer 922, a basement membrane 924, a compact layer 926, and a fibroblast layer 928. The epithelial layers 912, 922 can be adhered together with an adhesive or tissue glue 940 as described elsewhere herein. In such a configuration, the multi-layer dressing 900 can operate as a double-sided tape, where the stromal or fibroblast layer (e.g. layer 918) on one side adheres to an organ or tissue within the body, and the stromal or fibroblast layer (e.g. layer 928) on the opposing side adheres to another organ or tissue within the body. Such applications can be beneficial where, for example, it is desirable to keep two organs or tissues in proximity with one another following a surgical procedure.

It is observed that multi-layer amnion dressings typically are more rigid than single-layer amnion dressings, and hence can provide improved handling characteristics. Relatedly, in some instances amnion dressings can be rolled into a "jelly roll" configuration and inserted into a cylindrical tube or trocar for placement within the patient. Because the back-to-back amnion dressing presents epithelial tissue on both outer sides of the generally planar or sheet-like configuration, the dressing can easily be rolled in either a clockwise or a counterclockwise jelly-roll prior to advancement through the applicator.

In some applications, multi-layer amnion dressings can be placed within a patient between muscle tissue and bone tissue, or between muscle tissue at one location and muscle tissue at an adjacent location. The dressings are well suited for use in providing a barrier for any type of surgical indication. For example, following a tumor removal procedure, application of the dressing to the patient can help to reestablish a barrier at the surgical site. Dressings according to embodiments of the present invention are also well suited for use in multi-stage revision surgery procedures. Due at least in part to beneficial tensile strength and suturability characteristics, exemplary dressings can be sutured into place during surgery, so that the dressings remain in their desired locations following surgery.

As discussed elsewhere herein, multi-layer tissue compositions may include one or more tissue layers. For example, exemplary tissue compositions may include two or more layers of amnion tissue. As also discussed elsewhere herein individual tissue layers of a multi-layer tissue composition may be treated with glutaraldehyde, such that in some cases a single layer of the multi-layer tissue composition may be treated with glutaraldehyde, and in some cases more than one layer of the multi-layer tissue composition may be treated with glutaraldehyde.

Figure 14:
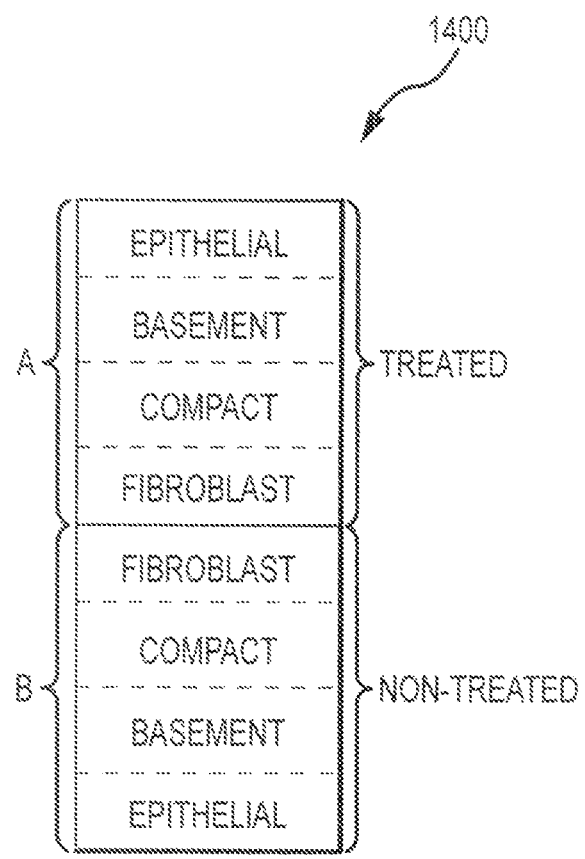
FIGS. 14, 15, and 16 depict aspects of amnion dressing compositions and methods of their manufacture, according to embodiments of the present invention.

FIG. 14 depicts aspects of a multi-layer tissue composition or patch 1400 according to embodiments of the present invention. As shown here, the tissue composition includes a first amnion layer (A) having epithelial, basement, compact, and fibroblast regions. Further, the tissue composition includes a second amnion layer (B) having epithelial, basement, compact, and fibroblast regions. The respective fibroblast regions can be coupled together or otherwise in contact with one another as discussed elsewhere herein. In the embodiment depicted here, amnion layer (A) is treated with glutaraldehyde, and amnion layer (B) is not treated with glutaraldehyde. Hence, tissue layer (A) can be considered as a treated layer, and tissue layer (b) can be considered as a non-treated layer. Layer (A) can be treated with any of the glutaraldehyde processing protocols as discussed elsewhere herein. Accordingly, the multi-layer tissue composition 1400 can provide a construct wherein different layers within the composition have been subjected to different treatment protocols. As depicted here, the composition 1400 is provided with two opposing epithelial outer layers, and the inner stromal sides are sandwiched together. The individual layers (A, B) can be prepared according to harvesting and preparation techniques as discussed elsewhere herein.

In some instances, a layer of a multi-tissue composition that is not treated with glutaraldehyde may be exposed to one or more growth factors. For example, the non-treated layer (B) shown in FIG. 14 may be soaked in or exposed to a solution or preparation containing one or more growth factors, including but not limited to IGF, FGF, PDGF, TGF, EDF, and cytokines. For example, the non-treated layer may be soaked in a high concentration solution containing such growth factors. The growth factors can be associated with or incorporated into the non-treated layer. In use, the growth factors can help contribute to healing provided by the multi-tissue composition.

Without being bound by any particular theory, it is believed that the absence of a glutaraldehyde treatment for the non-treated layer can help to preserve the presence of therapeutic components within or associated with the non-treated layer, including cells of the non-treated layer, such as stem cells, pluripotent cells, multipotent cells, and the like.

Figure 15:
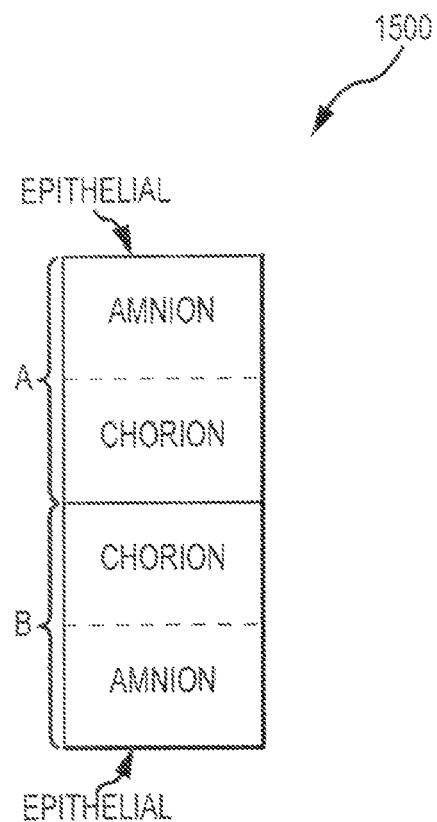

As discussed elsewhere herein, when the amnion layer is separated from the chorion layer, an asymmetrical tissue is produced having an epithelium layer on one side and a fibroblast layer on the opposite side. As shown in FIG. 15, in some instances a multi-layer tissue composition 1500 can be produced by leaving the chorion associated with the amnion. In this sense, tissue composition 1500 can be considered to include two layers of amniotic sac tissue, whereby the amniotic sac tissue includes an amnion layer and a chorion layer. The individual layers can be prepared according to harvesting and preparation techniques as discussed elsewhere herein.

It has been observed that such tissue compositions containing multiple layers of amniotic sac tissue remain intact during handling. That is, there is sufficient adherence between the chorion layers to keep the composition in one piece. For example, the opposing chorion layers were observed to remain adhered to one another, such that the weight or gravitational force of one amniotic sac layer pulling away from the other amniotic sac layer was not enough to cause the chorion layers to become separated. The outer epithelial portions of the amnion layers provide the multi-layer tissue composition 1500 with a beneficial lubricity. In some cases, the amnion tissue may have a higher degree of immune privilege than the chorion layer. Hence, it may be desirable to treat the chorion with an antibiotic or other immune response reduction agent. Relatedly, it may be desirable to process the chorion with a thorough wash treatment to reduce any immunogenicity.

In use, the presence of the chorion in the multi-layer composition can confer the material with a desirable degree of bulk and/or tensile strength. In some cases, one of the amniotic sac layers (amnion and chorion) may be processed with a glutaraldehyde treatment, and the other amniotic sac layer may not be processed with a glutaraldehyde treatment. In some cases, both amniotic sac layers, or multiple amniotic sac layers of a tissue composition, may be processed with a glutaraldehyde treatment. In use, the presence of chorion can help contribute to healing provided by the multi-tissue composition.

Figure 16:
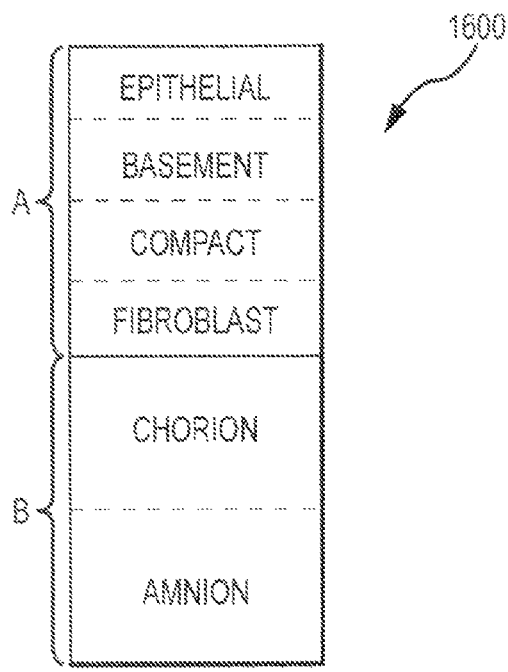

As shown in FIG. 16, in some instances a multi-layer tissue composition 1600 can be produced by removing the chorion associated with the amnion for one layer (A) of the issue composition, and by leaving the chorion associated with the amnion for another layer (B) of the tissue composition.

All patents, patent publications, patent applications, journal articles, books, technical references, and the like discussed in the instant disclosure are incorporated herein by reference in their entirety for all purposes.

It is to be understood that the figures and descriptions of the invention have been simplified to illustrate elements that are relevant for a clear understanding of the invention. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

While exemplary embodiments have been described in some detail, by way of example and for clarity of understanding, those of skill in the art will recognize that a variety of modification, adaptations, and changes may be employed. Hence, the scope of the present invention should be limited solely by the claims.

What is claimed is:

1. A method of manufacturing a multi-layer amnion tissue patch, the method comprising:
    obtaining a first amnion tissue layer having an epithelial layer, a basement membrane, a compact layer, and a fibroblast layer from which a spongy layer has been removed, the fibroblast layer including a loose network of reticulum, wherein the first tissue layer is treated with a glutaraldehyde exposure process;
    obtaining a second amnion tissue layer having an epithelial layer, a basement membrane, a compact layer, and a fibroblast layer from which a spongy layer has been removed, the fibroblast layer including a loose network of reticulum, wherein the second tissue layer is not treated with a glutaraldehyde exposure process;
    compressing the treated first amnion tissue layer with the untreated second amnion tissue layer so as to form the patch, such that the epithelial layers of the first and second amnion tissue layers define first and second opposing outer surfaces of the patch, respectively, wherein a compressed, coupled fibroblast region is disposed between at least a portion of the first and second opposing outer surfaces of the patch, and wherein the compressed, coupled fibroblast region comprises fibers of at least a portion of the first fibroblast layer entangled with fibers of at least a portion of the second fibroblast layer.

2. The method according to claim 1, wherein the first amnion tissue layer and the second amnion tissue layer are each part of a single piece of amnion tissue, and the compressing step comprises folding the single piece of amnion tissue over on itself so that a portion of the first amnion tissue layer at least partially overlaps a portion of the second amnion tissue layer.

3. The method according to claim 1, wherein the first amnion tissue layer and the second amnion tissue layer are each separate pieces of amnion tissue, and the compressing step comprises approximating the first and second layers so that a portion of the first amnion tissue layer at least partially overlaps a portion of the second amnion tissue layer.

4. The method according to claim 3, wherein the first amnion tissue layer is disposed in a first orientation, and the second amnion tissue layer is disposed in a second orientation that is angularly offset from the first orientation.

5. The method according to claim 4, wherein the first orientation is angularly offset from the second orientation by about 90 degrees.

6. The method according to claim 1, wherein the glutaraldehyde exposure process comprises exposing the first tissue layer to a glutaraldehyde solution for up to about 15 minutes.

7. The method according to claim 6, wherein the glutaraldehyde solution comprises 1% glutaraldehyde.

8. A multi-layer amnion tissue patch, comprising:
a first amnion tissue layer having an epithelial layer, a basement membrane, a compact layer, and a fibroblast layer from which a spongy layer has been removed, the fibroblast layer including a loose network of reticulum; and
a second amnion tissue layer having an epithelial layer, a basement membrane, a compact layer, and a fibroblast layer from which a spongy layer has been removed, the fibroblast layer including a loose network of reticulum;
wherein the epithelial layers of the first and second tissue layers define first and second opposing outer surfaces of the patch, respectively;
wherein a compressed, coupled fibroblast region is disposed between at least a portion of the first and second opposing outer surfaces of the patch, the compressed, coupled fibroblast region comprising fibers of at least a portion of the first fibroblast layer entangled with fibers of at least a portion of the second fibroblast layer; and
wherein the first amnion tissue layer is treated with a glutaraldehyde protocol and the second amnion tissue layer is not treated with a glutaraldehyde protocol.

9. A method of treating a patient with a multi-layer amnion tissue patch, the method comprising:
obtaining the multi-layer amnion tissue patch of claim 8; and
administering the multi-layer tissue patch to the patient.

10. The method according to claim 9, wherein the multi-layer tissue patch is administered to a patient tissue that is injured, damaged, crushed, sutured, inflamed, or ligated.

11. The method according to claim 9, wherein the administering step comprises a member selected from the group consisting of:
placing the patch at a surgical site within or on the patient's body,
placing the patch at a trauma site within or on the patient's body,
suturing the patch to the patient,
wrapping the patch about a patient nerve,
wrapping the patch about a patient tendon,
onlaying the patch over a patient bone defect,
placing the patch within a patient tarsal tunnel,
applying the patch to the patient's spine during a laminectomy procedure,
applying the patch to the patient's spine during an anterior lumbar interbody fusion procedure,
applying the patch to the patient's spine during a laminotomy procedure,
positioning the patch between two similar tissues,
positioning the patch between two dissimilar tissues,
positioning the patch at a dural tear,
positioning the patch at a knee cap so as to maintain a space in the knee cap area,
positioning the patch between two surfaces which are intended to remain separated after any healing phase,
contacting the patch with a patient peripheral nerve,
contacting the patch with a patient iliotibial band,
contacting the patch with a patient meniscus, and
contacting the patch with a patient extensor halgus longus tendon.

12. The method according to claim 9, wherein the first amnion tissue layer and the second amnion tissue layer are each part of a single piece of amnion tissue, the single piece of amnion tissue folded over on itself so that a portion of the first amnion tissue layer at least partially overlaps a portion of the second amnion tissue layer.

13. The method according to claim 9, wherein the first amnion tissue layer and the second amnion tissue layer are each separate pieces of amnion tissue, and a portion of the first amnion tissue layer at least partially overlaps a portion of the second amnion tissue layer.

14. The multi-layer tissue patch according to claim 8, wherein the compressed, coupled fibroblast region has an increased fiber density relative to a non-compacted fibroblast layer.

15. The multi-layer tissue patch according to claim 8, wherein the patch is wet and contained within a sealed pouch along with an amount of saline solution.

16. The multi-layer tissue patch according to claim 8, wherein the first amnion tissue layer and the second amnion tissue layer are each part of a single piece of amnion tissue, the single piece of amnion tissue folded over on itself so that a portion of the first amnion tissue layer at least partially overlaps a portion of the second amnion tissue layer.

17. The multi-layer tissue patch according to claim 8, wherein the first amnion tissue layer and the second amnion tissue layer are each separate pieces of amnion tissue, and a portion of the first amnion tissue layer at least partially overlaps a portion of the second amnion tissue layer.

* * * * *